US008753875B2

(12) United States Patent
Frimodt-Møller

(10) Patent No.: US 8,753,875 B2
(45) Date of Patent: Jun. 17, 2014

(54) COMPOSITIONS AND MEANS FOR DIAGNOSING MICROBIAL INFECTIONS

(75) Inventor: Niels Frimodt-Møller, Gentofte (DK)

(73) Assignee: Statens Serum Institut, Copenhagen S (DK)

( * ) Notice: Subject to any disclaimer, the term of this patent is extended or adjusted under 35 U.S.C. 154(b) by 965 days.

(21) Appl. No.: 12/198,542

(22) Filed: Nov. 4, 2008

(65) Prior Publication Data

US 2009/0068696 A1 Mar. 12, 2009

Related U.S. Application Data

(60) Provisional application No. 60/969,260, filed on Aug. 31, 2007.

(30) Foreign Application Priority Data

Aug. 31, 2007 (EP) .................................... 07115480

(51) Int. Cl.
C12M 1/00 (2006.01)
(52) U.S. Cl.
USPC ..................................................... 435/289.1
(58) Field of Classification Search
CPC .................................................... C12M 1/00
USPC ..................................................... 435/289.1
See application file for complete search history.

(56) References Cited

U.S. PATENT DOCUMENTS

| | | | |
|---|---|---|---|
| 5,512,450 | A | 4/1996 | Johnson et al. |
| 5,523,214 | A | 6/1996 | Horn |
| 5,534,415 | A | 7/1996 | Orenga |
| 5,635,367 | A * | 6/1997 | Lund ................................ 435/34 |
| 5,962,251 | A | 10/1999 | Rambach |
| 6,090,541 | A * | 7/2000 | Wicks et al. ........................ 435/5 |
| 6,136,554 | A | 10/2000 | Bochner |
| 6,251,624 | B1 | 6/2001 | Matsumura et al. |
| 6,350,588 | B1 | 2/2002 | Roth et al. |
| 6,750,038 | B1 | 6/2004 | Nakane |
| 2002/0076742 | A1 | 6/2002 | Chen et al. |

FOREIGN PATENT DOCUMENTS

| | | |
|---|---|---|
| WO | WO 99/18232 | 4/1999 |
| WO | WO 01/06000 A | 1/2001 |
| WO | WO 03/106696 A2 | 12/2003 |
| WO | WO 2004/050675 A1 | 6/2004 |

OTHER PUBLICATIONS

Cassar et al. "Comparison of *Salmonella* chromogenic medium with DCLS agar for isolation of *Salmonella* species from stool specimens", J Clin Microbio., 2003, 41(7):3229-3232.*
Watkinson et al. "Novel method for rapid assement of antibiotic resistance in *Escherichia coli* isolates from environmental waters by use of a modified crhomogenic agar", Applied and Environmental Microbiology, Apr. 2007, 73(7):2224-2229.*
SCM—Oxiod data sheet: 2 pages, 2001-2011.*
Bascomb et al. "Rapid antimicrobial susceptibility testing of gram-positive cocci using Baxter Microscan Rapid fluorogenic panels and autoSCAN-W/A" Path Biol., 1991, 39(5):466-470.*
Bullseye Urine Plate data sheet: 4 pages.*
Reissbrodt et al. "Assessment of a new selective chromogenic *Bacillus cereus* group plating medium and use of enterobacterial autoinducer of growth for cultural identification of *Bacillus* speices", J of Clin. Micro., 2004, 42(8):3795-3798.*
Miyanaga et al. "Detection of *Escherichia coli* in the sewage influent by fluorescent labeled T4 phage", Biochemical Engineering Journal, 2006, 29:119-124.*
Bill et al."Comparison of in vitro activity of cephalexin, cephradine, and cefaclor", Antimicrobial agents and Chemotherapy, 1977, 11(3):470-474.*
Zambon et al. "Serology of oral actinobacillus actinomycetemcomitans and serotype distribution in human periodontal disease" Infection and Immunity, 1983, 41(1):19-27.*
Yazid et al. "Antimicrobial susceptibility of bifidobacteria", Letters in Applied Microbiology, 2000, 31:57-62.*
DCLS data sheet: 1 page.*
Shigeo Yano et al., "Determination of Endotoxin in Injectable Antibiotic Preparations by the Chromogenic Assay Method Using a *Limulus* Reagent (*Tachypleus* Hemocyte Lystate) and a Chromogenic Substrate" Journal of Clinical Microbiology, Jan. 1986, vol. 23, No. 1, pp. 11-16.
Jack L. Perry et al., "Evaluation of Leukocyte Esterase Activity as a Rapid Screening Techique for Bacteriuria", Journal of Clinical Microbiology, May 1982, vol. 15, No. 5, pp. 852-854.
Indole Spot Reagent (1% Cinnamaldehyde), Dalynn Biologicals, Catalogue No. R140, 2 Pgs., Jan. 2002.
Heide J.K. Slade et al., "Effect of Oxygen Radicals and Peroxide on Survival After Ultraviolet Irradiation and Liquid Holding Recovery of *Bacteroides fragilis*", Journal of Bacteriology, Aug. 1981, vol. 147, No. 2, pp. 685-687.
Colina Jones et al., "Effect of Minimal Amounts of Thymidine on Activity of Trimethoprim-Sulfamethoxazole against *Staphylococcus epidermidis*", Antimicrobial Agents and Chemotherapy, vol. 31, No. 2, pp. 144-147, Feb. 1987.
R. Ferone et al., "Identification of Harper-Cawston Factor as Thymidine Phosphorylase and Removal from Media of Substances Interfering with Susceptibility Testing of Sulfonamides and Diaminopyrimidines", Antimicrobial Agents and Chemotherapy, Jan. 1975, vol. 7, No. 1, pp. 9-98.
Flexicult SSI Urinary Kit—Brochure, Statens Serum Institut, Kobenhavn 5 Denmark, 1st edition, Jan. 2007, 65888, pp. 1-27—In Color.
Walter E. Stamm et al., "Diagnosis of Coliform Infection in Acutely Dysuric Women", The New England Journal of Medicine, vol. 307, No. 8, Aug. 19, 1982, pp. 463-468.

(Continued)

*Primary Examiner* — Bin Shen
(74) *Attorney, Agent, or Firm* — Foley & Lardner LLP; Andrew S. Baluch

(57) ABSTRACT

The present invention pertains to the need for novel, reliable, fast and inexpensive approaches to diagnosing, including detecting and characterizing microbial infections in humans and animals or methods for detecting and characterizing microbial infections in various environments, such as in a food or feed sample. The present invention provides compositions, platforms, kits and methods for diagnosing, detecting and/or characterizing a microbial infection or contamination. In particular the present invention relates to such compositions, platforms, kits and methods for diagnosing, detecting and/or characterizing a urinary tract infection.

59 Claims, 4 Drawing Sheets

(56) References Cited

OTHER PUBLICATIONS

George G. Zhanel et al., "Antibiotic resistance in *Escherichia coli* outpatient urinary isolates: final results from the North American Urinary Tract Infection Collaborative Alliance (NAUTICA)", International Journal of Antimicrobial Agents 27 (2006) 468-475.

Sven Ferry et al., "Uricult and Sesicult Dipslides for Diagnosis of Bacteriuria and Prediction of Drug Resistance in Primary Health Care", Scand J Prim Health Care 1989; 7: 123-128.

Niels Frimodt-Moller et al., "Evaluation of calibrated 1 and 10 μl loops and dipslide as compared to pipettes for detection of low count bacteriuria in vitro", APMIS 108:523-530, 2000.

G. Kahlmeter, "An International Survey of the Antimicrobial Susceptibility of Pathogens from Uncomplicated Urinary Tract Infections: the ECO-SENS Project", Journal of Antimicrobial Chemotherapy (2003) 51, 69-76.

Edward H. Kass et al., "Pyelonephritis and Bacteriuria", Annals of Internal Medicine, vol. 56, No. 1, Jan. 1962, pp. 46-53.

K. B. Laupland et al., "Community-onset Urinary Tract Infections: A Population-based Assessment", Infection 35, 2007, No. 3, pp. 150-153.

C.E. Mabeck M.D., "Treatment of uncomplicated urinary tract infection in non-pregnant women" Postgraduate Medical Journal, Feb. 1972, 48, 69-75.

Tamara Rodriguez et al., "Standardization of *Neisseria meningitidis* Serogroup B Colorimetric Serum Bacterially Assay", Clinical and Diagnostic Laboratory Immunology, Jan. 2002, vol. 9, No. 1, pp. 109-114.

N. Frimodt-Moller et al., ICAAC Conference in USA, Sep. 2007. "Rapid Diagnosis and Susceptibility Testing of Urinary Tract Pathogens in General Practise".

"Diagnosis of infections of the Urinary Tract", Folder with cover letters. Aug. 2006.

N. Frimodt-Moller et al., "Screening for bakteriuri I laboratoriet: autotrak, teststrimler og mirkoskopi sammenlignet med dyrkning", Ugeskr Laeger 1989, 151: 3062-3064.

* cited by examiner

10³ cfu/ml      10⁴ cfu/ml

10⁵ cfu/ml      10⁶ cfu/ml

10⁷ cfu/ml

E. coli

COMPOSITIONS AND MEANS FOR DIAGNOSING MICROBIAL INFECTIONS

CROSS-REFERENCE TO RELATED PATENT APPLICATIONS

European Patent Office Priority Application 07115480.1, filed Aug. 31, 2007 including the specification, drawings, claims and abstract, is incorporated herein by reference in its entirety. This application claims priority from Provisional Application U.S. Application 60/969,260, filed Aug. 31, 2007, incorporated herein by reference in its entirety.

TECHNICAL FIELD OF THE INVENTION

The present invention relates to compositions, platforms, kits and methods for diagnosing, detecting and/or characterising a microbial infection or contamination. In particular the present invention relates to such compositions, platforms, kits and methods for diagnosing, detecting and/or characterising a urinary tract infection.

BACKGROUND OF THE INVENTION

Urinary Tract Infections (UTI)

Urinary tract infection is one of the most common infections in general practice as well as the most common nosocomial infection in the western world. The overall prevalence is 3-5% and the incidence 18/1,000 inhabitants per year[1].

Infections are most prevalent in females (six-fold higher risk than in men), which is usually explained by the fact that the opening of the urethra lies in direct contact with the vaginal flora and the urethra is fairly short in women in contrast to the 4-5 times longer and therefore protected urethra in men. Regarding age groups, infections are most common early, i.e. below the age of one, and late in life, i.e. >60 years of age.

Although most infections are uncomplicated lower UTI, i.e. bladder infections, which often cure themselves without antibiotic treatment, UTI can also be complicated with ascending renal infections which can spread to the blood leading to septicemia with septic shock. Around 50% of *Escherichia coli* bacteraemias have the urinary tract as focus, and the mortality is around 20% for these infections in spite of effective antibiotics. Renal impairment with uraemia and dialysis treatment is caused by chronic urinary tract infections in more than a third of cases. Operative procedures and other iatrogenic manipulations of the urinary tract such as cystoscopy, catheterisation etc. results in a significant amount of infections, e.g. bladder catheterisation leads to bacteriuria in 30-50% of patients after a week and almost 100% after a month.

Pathogenesis and Etiology:

UTI can be caused by virus such as adenovirus and by flagellates such as *Trichomonas vaginalis* but the majority of infections (>98%) are caused by bacteria, which in most cases stem from the patients' own rectal flora. Due to chance or low hygiene bacteria can spread from the rectum and anus via the perineum to the vagina, where they can colonize the vagina and especially the area around meatus urethrae externae. From this point they gain access to the urethra helped by factors such as e.g. low temperatures inhibiting local immune function or by physical factors such as intercourse. If the bacteria contain specific virulence factors, which help them to adhere to the mucous membranes in the urethra and the bladder, they can penetrate into and through the epithelium and into the tissue underneath. An infective process ensues with intracellular micro-colony formation, apoptosis of the epithelial cells and release of cell material and bacteria into the bladder lumen with risk of renewed infection. In many cases the immune system will by and large remove the bacteria and restore normal function of the bladder wall tissue, but the bacteria in the bladder lumen can given time enough also ascend via the ureters to the renal pelvis, where they can spread further to the medulla and the cortex of the kidneys causing pyelonephritis, peri- or intrarenal abscess or other calamities.

The immune reaction can be seen as increasing numbers of leucocytes, mostly granulocytes, in the urine and in the tissues involved. Specific antibodies against the intruder can also be measured after 2-3 weeks in most persistent cases.

*E. coli* is the main culprit causing 60-90% of UTIs since this bacterium often holds the virulence factors necessary for causing UTI, i.e. adherence properties (fimbriae or pili with special predilection for receptors on the bladder epithelium), cell movement (flagellae) and a vast amount of other virulence factors, which enables the bacteria to circumvent the immune function and penetrate into human tissue. The rest of the infections are caused by other Enterobacteriaceae (*Klebsiella* and *Enterobacter* spp., *Proteus* spp.) and some Gram-positive bacteria (Enterococci, *Staphylococcus saprophyticus, Aerococcus* spp.) and more rarely *Candida* spp. The possible role of *Mycoplasma* and *Ureaplasma* spp in UTI is still under debate.

Bacteria may be found in the urine of a patient who does not have symptoms or other signs (e.g. leucocyturia), i.e. so-called asymptomatic bacteriuria. This is particularly common in elderly patients and a prevalence of 10-15% has been found in several studies.

Clinical Presentation:

The bladder infection leads to local pain, which can be felt behind the pubic bones or perhaps in the loins—but this is often a sign of renal involvement, as well as pain during voiding. Also, the irritation in the bladder will lead to frequent voiding. Fever can evolve although this is more common in case of pyelonephritis. The urine will change colour and turbidity to dark, cloudy and some times with hematuria, i.e. presence of erythrocytes due to minor bleeding from the scarred bladder epithelium. If bacteremia ensues the patient will develop signs of sepsis with general pain and malaise, high fever and shivering.

Even with uncomplicated UTI the patient is so invalidated by the condition that she (or he) will stay home from work and seek medical attention.

Diagnosis of UTI

Since the urinary tract is usually sterile with low numbers of leucocytes, the presence of bacteria and increased numbers of leucocytes is indicatory of infection. The diagnosis of UTI is based on the typical symptoms as well as presence of bacteria and increased numbers of leucocytes in a sterilely obtained urine sample. Due to the common colonisation of the external part of the urethra, it is difficult to obtain a sample during voiding without contamination of the sample. To avoid this contamination the best way to obtain a sterile urine sample is by suprapubic puncture, or via a bladder catheter or in case of renal pelvis infection via a percutaneous nephrostomy. But since these latter methods are rather cumbersome and often painful for the patient in the large majority of cases and also demands hospital admission, in most cases the urine is collected as a Mid Stream Urine (MSU), i.e. the meatus is cleaned with a cotton swab wetted with sterile saline, the patient then voids a small first part of the urine to cleanse the urethra and then voids—mid-stream—a sample collected in a sterile container—to end by voiding the rest of the urine volume in the toilet.

Other samples such as swabs from the urethra or blood cultures are also taken on indication of urethritis (e.g. gonorrhoea) or bacteraemia.

Quantitative Criteria for Diagnosis of UTI:

Due to the problems with contamination of the urine sample when taken as MSU and the subsequent evaluation of the results, and the fact that some patients may have asymptomatic bacteriuria it was in the 1950' ies found not the least in studies by Edward Kass[2], that in order to discern between an asymptomatic patient and a patient with pyelonephritis, at least $10^5$ bacteria/ml urine of one potential urinary pathogen (see above) must be present in two urine samples taken at least 24 h apart.

Later, it was found that counts down to $10^3$ bacteria/ml of urine of a typical urinary pathogen (see above) is indicative of infection in patients, who have typical symptoms of UTI[3], i.e. the Kass-criteria[2] are used for patients with asymptomatic bacteriuria.

Currently used methods of diagnosing bacteria in the urine:

a) Direct methods

1. Microscopy: Bacteria can be visualized in the urine sample by either phase contrast microscopy of a wet smear, or by simple light microscopy of a Gram-coloured preparation. In the wet smear, the form and possible movement of the bacteria can be seen but naturally not the Gram-type of the bacteria. This can be discerned by the light microscopy of the Gram-stain, and in both cases leucocytes can be seen and roughly quantified. The problem with microscopy is the lack of specificity, i.e. only a presumptive bacterial diagnosis can be given, and the sensitivity i.e. bacteria can only be visualized when present in numbers of at least $10^5$ bacteria/ml of urine. Furthermore, microscopy will not reveal the antibiotic susceptibility of the bacteria. Phase contrast microscopy has a positive predictive value of 58% as related to quantitative culture with $\geq 10^5$ bacteria/ml as criteria for UTI[4].

2. Culture: The gold standard of diagnosis of UTI. In the laboratory this is performed by a quantitative culture, i.e. a standardized loop applying 1 or 10 µl urine on an agar plate. This allows quantification of bacteria by counting the number of colonies (colony forming units, CFU) on the incubated plate. If low numbers of bacteria are anticipated (e.g. suprapubic puncture or catheter sample) up to one ml of urine may be cultured allowing the counts of down to 1-2 CFU/ml urine. The culture can lead to further diagnosis of the bacteria by biochemical and other types of laboratory workup. Furthermore, a susceptibility test can be performed. Sensitivity of the method is by definition 100%, but in some cases bacteria may not grow if special media, atmosphere or temperature conditions are not used (some Aerococcus strains may only grow on blood agar and in $CO_2$), or if the patient has started antibiotic treatment bacteria may not grow due to antibiotic suppression. The specificity is not 100%, since the positive culture may still contain contaminants—the result should be combined with the symptoms and signs as well as the presence of increased numbers of leucocytes in the urine. The quantitative loops have a variation of +/−½ log CFU/ml, which means that only a rough estimate of the counts can be made[5]. The disadvantage of quantitative cultures in the laboratory is that the urine must be kept in a condition, where the bacteria do not multiply prior to culture; this can be obtained by cooling the urine during transportation (i.e. <4° C.) or by the use of transport media, which preserve the bacteria without promoting growth, e.g. by using boric acid. Boric acid containing tubes for transportation have therefore become popular in recent years, but this method carries the inherent problem of boric acid being toxic, e.g. carcinogenic to humans.

Other culture methods: Dipslides with a plastic plate skeleton carrying agar media on one or both sides that are dipped into the urine have been used for 20-30 years (e.g. Uricult (Orion)). The advantage of these is the ease of inoculation and that the direct inoculation can be quantified by comparing the bacterial growth with pictures of dipslides used for cultures with known quantities of bacteria. The dipslide can also be used as a transport medium. A susceptibility test has been developed, where antibiotic containing discs are placed on the agar surfaces after inoculation (e.g. Sensicult (Orion)). The positive predictive value (PPV) of the susceptibility test has in some cases been as low as 0.6, which can be explained by the lack of standardized inoculum and difficulty in interpreting a zone around the disc on a rounded surface, as the agar plate is not completely flat. Also, the small surface of the dipslide (i.e. approx. 2×5 cm) makes it difficult to evaluate the growth characteristics of bacteria, and especially whether there are more than one species. Furthermore, evaluation of susceptibility is difficult without the knowledge of the bacterial species. A dipslide with chromogenic agar on one of the sides (DipStreak) has recently been marketed by Novamed in Israel.

3. Other methods: During the later years several methods have been tried for quantifying bacteria in urine such as turbidity measurements by spectrophotometry, cytocentrifugation, ATP-measurement and others. So far, to our knowledge, none of these have been applied in routine laboratories and especially not so in primary care due to their cost and demand for technical skill.

b) Indirect methods:

1. Dipstick for nitrite and leucocyte-esterase: Determination of nitrite in the urine is used for diagnosis of UTI, since this substance can only be present if nitrate-reductase producing bacteria are present in the urine. Nitrate stems from protein-metabolism and is found in urine in varying concentrations depending on the intake of protein the day up to the sampling. Nitrite can be removed, however, if there are bacteria present, which produce nitrite-reductase (e.g. *E. coli* can contain both types of enzymes). The test is not very sensitive, since the reaction needs about 3 hours of incubation, some bacteria produce nitrite-reductase, and some urinary pathogens do not produce nitrite-reductase at all, e.g. staphylococci. The leucocyte-esterase test is more relevant, since it is the easiest way to prove the presence of leucocytes; the enzyme can only stem from leucocytes, and the amount of enzyme is correlated to the numbers of leucocytes. Whole leucocytes lyse easily and rapidly, which means that the urine microscopy for leucocytes must be performed within an hour after sampling in order to achieve a relevant quantitative microscopy, while the enzyme test can be performed several hours later due to the stability of the enzyme. The presence of leucocytes, however, is only predictive of infection in 50% of patients, since leucocyturia can be found in many patients without infection. Together, the test for the two enzymes combined (i.e. either one or both positive) has a rather low PPV (60-80%) due to the above mentioned factors.
2. Symptoms alone: In many cases in general practice, the general practitioner (GP) will initiate treatment based on symptoms alone.

This can be due to reservations against diagnostic workup due to cost, geography or tradition, knowledge of susceptibility of the pathogens and/or use of broad spectrum antibiotics suspected to cover all possible pathogens.

Treatment of UTI:

In 30% of cases of uncomplicated UTI, the infection will be self-curable, i.e. disappear without antibiotic treatment[6]. But in most cases and especially in complicated cases i.e. all other patients than women in the age group 14-60 years of age, antibiotic treatment is the standard. Depending on the condition and the antibiotic used the uncomplicated infection will be cured in 3-7 days, while pyelonephritis needs 10-14 days of treatment, and the more chronic cases longer duration of treatment, which can in some cases be months to years. The effect depends upon the susceptibility of the bacterial pathogens[6,7]. The standard test performed in a laboratory takes time, especially when the disc susceptibility test is performed, since this test is based on several conditions being kept within certain limits (inoculum, incubation time, reading of the test, incubation atmosphere etc.). The most important factor is the inoculum, which must be within certain narrow limits to ensure quality of the test, why it is difficult to perform a meaningful disc diffusion susceptibility test directly on the primary urine sample, since the exact number of bacteria is unknown.

WO 99/18232 (by Chen et al) provides a multi-compartment assay device based on the combined use of medium capable of sustaining growth of total microbial organisms, a medium which is selective for the particular target organism and a medium which comprises an antimicrobial susceptibility interpretation medium. The application teaches the use of liquid medium and does not suggest a set-up which allows differentiation between the presence of multiple groups and/ or strains of micro-organisms in the same sample and determination of the antimicrobial susceptibility of each group or strain of said micro-organisms.

Later Chen et al in WO03106696 discloses methods and devices for the detection of pathogenic microorganisms and their antimicrobial susceptibility. The use of a fluorescent or chromogenic substrate can be included to get a visual signal of the presence of the microorganism, but the use of several different substances to determine different species is not mentioned.

WO0106000 discloses a test media for identification and differentiation of enterobacteriaceae. The medium comprises an antibiotic to prevent growth of other microorganisms than enterobacteriaceae.

U.S. Pat. No. 6,750,038 describes a rapid antibiotic susceptibility test. The use of a chromogene is not used to identify the microorganisms.

U.S. Pat. No. 6,251,624 discloses an apparatus and method for detecting, quantifying and characterizing microorganisms. Antibiotic susceptibility is tested by growth zone inhibition.

WO2004050675 discloses a multichamber growth plate with selective broth for identification of particular microorganisms and with antibiotics in the media for testing susceptibility Hence, an improved technology for diagnosis, detection and characterisation of microbial infections or contamination, offering the possibility of differentiating between such multiple groups and/or strains of micro-organisms would be advantageous. In particular, such a technology would be advantageous if provided in the form of a platform which is efficient, reliable and possible to manufacture at a reasonable cost.

SUMMARY OF THE INVENTION

Thus, an object of the present invention relates to compositions, platforms, kits and methods for diagnosing, detecting and/or characterising a microbial infection or contamination.

Thus, one aspect of the invention relates to a composition comprising a semi-solid microbial growth medium, two or more chromogenic or fluorescent substances (or substrates), and an antimicrobial.

Another aspect of the present invention relates to a platform comprising a composition according to the invention.

Yet another aspect of the present invention provides a kit comprising a composition according to the invention.

Further aspects of the invention provide:

A kit comprising a platform according to the invention.

Use of a compositions according to the invention, in the detection and or/identification of pathogenic, in particular uropathogenic microorganisms.

Use of a composition according to the invention, in detection and/or diagnosis of infections selected from the group consisting of urinary tract infections, skin and soft tissue infections, infections with *S. aureus* (including methicillin resistant *S. aureus*), infections with meningococci, infections with gonococci, infections with streptococci including infections with pneumococci.

A composition according to the invention, for use in detection and/or diagnosis of infections selected from the group consisting of urinary tract infections, skin and soft tissue infections, infections with *S. aureus* (including methicillin resistant *S. aureus*), infections with meningococci, infections with gonococci, infections with streptococci including infections with pneumococci.

A method of diagnosing, detecting and/or characterising a microbial infection or contamination comprising the steps of:
 i) providing a sample with a possible microbial infection or contamination; and
 ii) contacting said sample with a platform according to the invention.

A method of diagnosing, detecting and/or characterising a microbial infection or contamination comprising the steps of:
 i) providing a sample with a possible a microbial infection or contamination; and
 ii) contacting said sample with a test composition (such as two or more test compositions), comprising a semi-solid microbial growth medium, two or more chromogenic or fluorogenic substances (or substrates), and an antimicrobial, and with a control composition, comprising said semi-solid growth medium and said two or more chromogenic or fluorogenic substances (or substrates) but not comprising any antimicrobial/said antimicrobial.

A method of manufacturing the composition according to the invention, comprising the step of combining a semi-solid microbial growth medium, two or more chromogenic substances (or substrates), and an antimicrobial.

A method of manufacturing the platform according to the invention, comprising the step of combining a semi-solid microbial growth medium, two or more chromogenic substances (or substrates), and an antimicrobial.

A method of manufacturing the diagnostic kit according to the invention, comprising the step of combining a semi-solid microbial growth medium, two or more chromogenic substances (or substrates), and an antimicrobial.

TABLE A

Figure 1A:
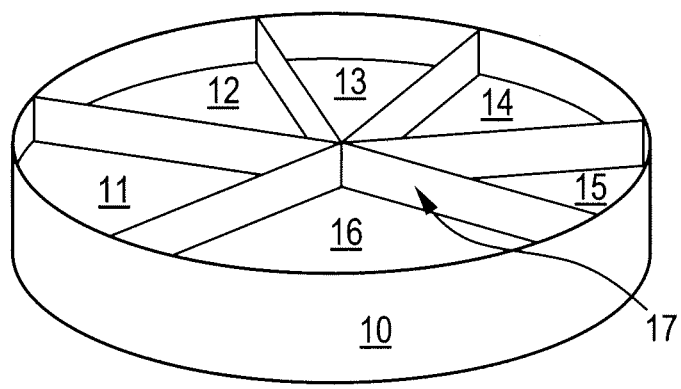
FIG. 1 shows two presently preferred embodiments relating to the platform according to the present invention: according to FIG. 1A the platform comprises an indentation (10) being capable of acting as a receptacle for a sample with a possible a microbial infection or contamination. The indentation is divided into separate compartments (11, 12, 13, 14, 15, and 16), by means of one or more integrated dividing members (17). Each compartment contains a composition comprising a semi-solid microbial growth medium, two or more chromogenic or fluorogenic substances or substrates and an antibiotic; or a composition that comprises a semi-solid microbial growth medium, two or more chromogenic or fluorogenic substances or substrates, but does not comprise an antimicrobial. According to FIG. 1B the platform comprises multiple indentations (18), each indentation being capable of acting as a receptacle for a sample with a possible microbial infection or contamination. Each indentation contains a composition comprising a semi-solid microbial growth medium, two or more chromogenic or fluorogenic substances or substrates and an antibiotic; or a composition that comprises a semi-solid microbial growth medium, two or more chromogenic or fluorogenic substances or substrates, but does not comprise an antimicrobial.

| Bacterium | Colony size | Colony colour | Agar colour | Susceptibility = S or Resistance = R | | | | |
|---|---|---|---|---|---|---|---|---|
| | | | | Trimethoprim | Sulfamethizole | Ampicillin | Mecillinam | Nitrofurantoin |
| *E. coli* | Large | Red/brownish | — | S | R | R | S | S |
| *Klebsiella* spp. | Large, Fat | Dark blue | — | S | S | R | S | R |
| *Enterobacter* spp | Large | Dark blue | — | S | R | R | R | S |
| *Proteus mirabilis* | Large (swarm) | Light brown/Brown | Brown | S | S | S | R | S |
| *P. vulgaris* | Large (swarm) | Greenish brown | Brown | S | S | R/S | R | R/S |
| *Morganella* spp. | Large (swarm) | Light brown | Brown | S | S | R | R | R/S |
| *Citrobacter* spp. | Large | Green/greenish blue | — | S | S | R | S | S |
| *P. aureginosa* | Small | Greyish white/greenish | Greenish | R | R | R | R | R |
| *E. faecalis* | Small | Green/greenish blue | Dark ring around colony | S | R | S | S | R |
| *E. faecium* | Small | Greenish | Dark ring around colony | S | R | S | S | R |
| *S. saprophyticus* | Small | White/Reddish | — | S | S | S | S | S |
| *Candida* spp. | Large/small | White | — | R | R | R | R | R |

The present invention will now be described in more detail in the following.

DETAILED DESCRIPTION OF THE PREFERRED EMBODIMENTS

Definitions

Prior to discussing the present invention in further details, the following terms and conventions will first be defined:
Microbial In the present context the term "microbial" is to be interpreted broadly as meaning "pertaining to a microbe." The term "microbe" refers collectively to bacteria, fungi, archaea and protists.

Semi-Solid Growth Medium

The expression "semi-solid growth medium" as used herein refers to a growth medium which allows micro-organisms to form colonies on its surface, such as a medium which has a gel-like appearance or is in the form of a gel, a gel being a colloidal system in which a porous network of interconnected particles spans the volume of a liquid medium. It is further understood that a gel is mostly liquid in composition and thus exhibit densities similar to that of the particular liquid, however have the structural coherence of a solid. Preferably, the semi-solid growth medium as used herein is prepared by adding to a liquid growth medium a sufficient amount of a substance which melts when heated and solidifies when cooled again, such as gelatin or agar. It will be understood that the porous network of interconnected particles in the medium will allow nutrients and antimicrobial to diffuse through the medium to become available to the micro-organisms.

Growth Medium

In the context of the present invention the term "growth medium" refers to a substance in or on which microbes can grow. The term in particular comprises nutrient broth (liquid nutrient medium) or Lysogeny Broth (L-B medium) and agar, which are the most common growth media for microbes.

Likewise, the term covers liquid medium in which microbes may grow in suspension, as well as semi-solid medium as defined above, allowing microbes to form colonies on its surface. The term "growth medium" also comprises specialized media which are sometimes required for growth of certain microorganism including fastidious organisms, requiring specialized environments due to complex nutritional requirements.

In general, a growth medium will comprise a carbon source such as glucose or succinate for bacterial growth, water, various salts provide essential elements needed for microbial growth, such as magnesium, nitrogen, phosphorous, and sulfur to allow the bacteria to synthesize protein and nucleic acid, and a source of amino acids and nitrogen (e.g., beef, yeast extract).

It is also to be understood that the term "growth medium" includes defined media, also known as chemical defined media, as well as undefined media, also known as basal or complex media. A defined medium for microbes will have known quantities of all ingredients, including trace elements and vitamins required by the microbe and especially a defined carbon source such as glucose or glycerol, and a defined nitrogen source such as an ammonium salt or a nitrate. An undefined medium on the contrary, has some complex ingredients, such as yeast extract or casein hydrolysate, which consist of a mixture of many chemical species in unknown proportions.

Chromogenic Substrate

In the context of the present invention the terms "chromogenic substrate," "chromogenic substance" and "chromogen" are used interchangeably referring to a precursor of a biochemical pigment. It is to be understood that, in particular, the chromogen may be a substrate, compound or substance, which when metabolized by a microbe produces a characteristic colour or pigment that is useful as a means of detection and/or identification of said microbe.

Fluorogenic Substrate

The term "fluorogenic substrate" is used interchangeably with "fluorogenic substance," referring to a precursor of a fluorescent compound. A fluorescent compound is a compound in which the molecular absorption of a photon triggers the emission of another photon with a longer wavelength and wherein the energy difference between the absorbed and emitted photons ends up as molecular vibrations or heat. In particular, the absorbed photon is in the ultraviolet range, and the emitted light is in the visible range. Hence detection of fluorescent compounds may typically be performed by exposing them to ultraviolet light (UV light) and then subsequently registering the light (often visible light) which is emitted by the fluorescent compound. It is to be understood that, in particular, the fluorescent substrate may be a substrate, compound or substance, which when metabolized by a microbe emits light that is useful as a means of detection and/or identification of said microbe.

Antimicrobial

In the present application the terms "antibiotic" and "antimicrobial" are used interchangeably to define a chemical compound that inhibits or abolishes the growth of microorganisms, such as bacteria, fungi or protozoans, that is, a chemical compound with anti-bacterial, anti-fungal, and/or anti-parasitical activity. The term includes antibiotic or antimicrobial compounds produced and isolated from living organisms, for example, the penicillin-class produced by fungi in the genus *Penicillium* or streptomycin from bacteria of the genus *Streptomyces*. The terms also include antibiotic or antimicrobial compounds obtained by chemical synthesis, such as sulfonomide drugs.

The terms in particular include anti-bacterial antibiotics, which are antibiotics that do not have activity against viruses, fungi and other non-bacterial microbes. The anti-bacterial antibiotics include bactericidal antibiotics, which destroy bacteria, and bacteriostatic antibiotics which prevent bacteria from multiplying. The anti-bacterial antibiotics further include "narrow-spectrum" antibiotics which target particular types of bacteria, such as Gram negative or Gram-positive bacteria, and broad spectrum antibiotics which affect a wide range of bacteria. Likewise, the anti-bacterial antibiotics include antibiotics for ingestion as well as antibiotics for intravenous administration which are often used to treat serious infections such as deep-seeded systemic infections, and antibiotics for topical administration. The anti-bacterial antibiotics comprise antibiotics within the following presently recognised classes: Aminoglycosides, Ansamycins, Beta-lactam antibiotics, (including the carbacephem, carbapenems, cephalosporins (first, second, third and fourth generations), monobactams and penicillins) Glycopeptides, Macrolides, lincosamides, Polypeptides, Quinolones, Sulphonamides, Tetracyclines, Cyclic lipopeptides, Glycylcyclines, Oxazolidinones, diaminopyrimidines, Nitrofurans, Rifamycins, antibiotic peptides, amphenicols, nitroimidazoles, streptogramins and phosphomycins.

Aspects and Embodiments of the Invention

In a first and broadest aspect, the invention provides a composition comprising a semi-solid microbial growth medium, two or more chromogenic or fluorescent substances or substrates, and an antimicrobial. The fact that a semi-solid microbial growth medium is employed according to the present invention has the advantage that microbial growth can be observed as single colonies on the surface of said medium. The combined use of chromogenic or fluorescent substances or substrates offers the possibility of distinguishing multiple types or species of microorganisms growing on the medium by the colour of the pigment or fluorescence produced in the colonies. Simultaneously, it is possible to determine the sensitivity of each microbial type or species against the antimicrobial present in the composition according to the invention.

Another advantage of the present invention is that when the platform is used to test urine for infections the number of colonies formed on the semi-solid microbial growth medium directly correlates with the number of bacteria per volume of urine added to the platform. Thereby making it easy to determine the concentration of bacteria in the urine.

In a preferred embodiment of the present invention, the semi-solid medium comprises tryptophan. The advantage of including tryptophan is that it enables easy detection of Enterobacteria of the *Proteus*-Morganella-Providencia and at the same time tryptophan does not interfere with determination of antibiotic susceptibility.

In another preferred embodiment, the semi-solid medium in the composition according to the invention comprises a galactose polymer (Agar-agar) or Gelatin.

Preferably the composition according to the invention comprises a microbial growth medium selected from the group consisting of: Iso-sensitest agar, Danish Blood Agar, Discovery medium and Mueller-Hinton medium. For those media which do not inherently comprise tryptophan it may be a further advantage to include tryptophan in these media. The concentration of tryptophan in the medium may be between 0.25-3.0 g/liter.

The Iso-sensitest agar is currently available from Oxoid and its composition is specified in The Oxoid Manual 1998. The Iso-sensitest agar is composed by 11 g/l Hydrolysed casein, 3 g/l Peptones, 2 g/l Glucose, 3 g/l Sodium Chloride, 1 g/l soluble starch, 2 g/l Disodium hydrogen Phosphate, 1 g/l Sodium Acetate, 0.2 g/l Magnesium glycerophosphate, 0.1 g/l Calcium gluconate, 0.001 g/l cobaltous sulphate, 0.001 g/l Cupric sulphate, 0.001 g/l Zinc sulphate, 0.001 g/l Ferrous Sulphate, 0.002 g/l Magnesium Chloride, 0.001 g/l Menadione, 0.001 g/l Cyanobalamin, 0.02 g/l L-Cysteine hydrochloride, 0.02 g/l Tryptophan, 0.003 g/l pyridoxine, 0.003 g/l pantothenate, 0.003 g/l nicotinamide, 0.0003 g/l Biotin, 0.00004 g/l Thiamine, 0.01 g/l Adenine, 0.01 g/l Guanine, 0.01 g/l Xanthine, 0.01 g/l Uracil, 8 g/l agar, in distilled water.

As for the Danish Blood Agar this is known by the skilled person to have the following composition: 2 g Na2HPO4.12H2O, 625 g tryptone, 250 g starch, 833.6 g Potassium Chloride, 2.5 g detergent, 74.8 g meat broth (Oxoid CM975K), 800 g D(+)Glucose-monohydrate, 1.75 g Xanthin, 1.75 g Guanin, 17.5 g Magnesium Sulphate 7H2O, 19.2 g CaCl2.2H2O, 2,720 g Agar, 5 N HCl to pH 7.4, solution of vitamins, and 12.5 l horse blood per 250 liter distilled water.

The Discovery medium is manufactured by Oxoid (product code CM 1087). According to the manufacturer the medium has the following composition: 14.5 g/l Peptone, 2 g/l glucose, 5.5 g/l salt mix, 1 g/l Soluble starch, 1.5 g/l chromogenic mix, and 8 g/l Agar.

The Mueller-Hinton medium comprises 2 g/l Beef extract powder/beef extract, 17.5 g/l Acid Digest of Casein, 1.5 g/l starch and 17 g/l Agar.

It is to be understood that some variation in the amount of each component in said medium will be tolerated; in general a variation of ±20% will be tolerated. However, as the skilled person will know certain components may be varied to an even larger extent: the amount of agar may be varied substantially such as from 4-25 g/l without significantly altering the performance of the medium. It is thus generally preferred that the medium in the composition according to the invention comprises from 4-25 g/l of a galactose polymer.

These media, together with other suitable media are characteristic in offering great reliability when used for determining sensitivity towards antimicrobials. Such reliability is not seen for all media as some media comprise compounds which interfere with the antibiotics and thereby affects the ability to use these media for testing for antibiotic susceptibility. The great reliability is witnessed for instance by fact that on these media:

i) the addition of 16 mg/l ampicillin causes a reduction in the growth of/numbers of colonies formed by reference strain *Escherichia coli* ATCC 25922 of at least 5 logCFU/ml, as determined after contacting the composition with a suspension containing $10^5$ CFU/ml and incubating the composition for 18-24 hours at 37° C. and at ambient atmosphere;

ii) the addition of 32 mg/l nitrofurantoin causes a reduction in the growth of/numbers of colonies formed by reference strain *Staphylococcus saprophyticus* ATCC 49907 of at least 4 log CFU/ml, as determined after contacting the composition with a suspension containing $10^5$ CFU/ml and incubating the composition for 18-24 hours at 37° C. and at ambient atmosphere;

iii) the addition of 700 mg/l sulphamethizole causes a reduction in the growth of/numbers of colonies formed by reference strain *Escherichia coli* ATCC 25922 of at least 3 log CFU/ml, as determined after contacting the composition with a suspension containing $10^5$ CFU/ml and incubating the composition for 18-24 hours at 37° C. and at ambient atmosphere iv) the addition of 16 mg/l trimethoprim causes a reduction in the growth of/numbers of colonies formed by reference strain *Escherichia coli* ATCC 25922 of at least 3 log CFU/ml, as determined after contacting the composition with a suspension containing $10^5$ CFU/ml and incubating the composition for 18-24 hours at 37° C. and at ambient atmosphere v) the addition of 16 mg/l mecilinam causes a reduction in the growth of/numbers of colonies formed by reference strain *Escherichia coli* ATCC 25922 of at least 5 log CFU/ml, as determined after contacting the composition with a suspension containing $10^5$ CFU/ml and incubating the composition for 18-24 hours at 37° C. and at ambient atmosphere.

In further embodiments the microbial growth medium is a selective medium capable of applying a selective pressure to organisms growing on it, such as a medium which is selective for Gram-negative bacteria or for Gram-positive bacteria.

The semi-solid media may further comprise sulpha inhibitors and/or metal ions as they may affect the antibiotic susceptibility. For example variations in the concentrations $Mg^{2+}$ or $Ca^{2+}$, may affect results of aminoglycoside and tetracycline tests with *Ps. aeruginosa*. Furthermore, excess zinc ions may reduce zone sizes of carbapenems. Excessive cation content will reduce antibiotic activity, whereas low cation content may result in enhanced activity. The $Ca^{2+}$ and $Mg^{2+}$ ions may in particular be present in the semi-solid medium in the form of soluble salts. Sulfonamide is inhibited by thymidine, which bacteria can use and therefore grow in spite of sulfonamide. The presence of thymidin-phosphorylase will inhibit thymidine and thus restore the function of sulfonamide. The concentration needed of thymidine-phosphorylase will depend on the concentration of thymidine in the medium.

Another parameter of the semi-solid media is the concentration of thymidine as this may affect testing of trimethoprim and methicillin-resistant staphylococci. Most agar media contain small amounts of sulphonamide and trimethoprim antagonists that may affect the results of susceptibility testing (especially if blood is not added) with low antibiotic content in the medium. Hence in a particular embodiment Susceptibility test media should contain less than 0.03 mg/l thymidine, otherwise small colonies are seen on the trimethoprim agar. If the medium contains slightly more thymidine than recommended, it is possible to reduce the concentration by adding thymidine-phosphorylase: 0.025 to 0.1 IU enzyme/ml medium or 5% haemolysed horse blood, which contains the same enzyme.

Whereas the presence of only one antibiotic in the composition according to the invention may be desirable in respect of some antibiotics and for some purposes, the composition according to the invention may also comprise 2 or more antimicrobials, such as 3 or more antimicrobials, such as 4 or more antimicrobials, or such as 5 or more antimicrobials.

The composition according to the invention may be characterised in that the antimicrobial or, if more than one antimicrobial is present, that at least one of the antimicrobials, such as 2, 3, 4, 5 or more of the antimicrobials or all of the antimicrobials are selected from the group consisting of: Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Mezlocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin and Voriconazole.

A complete list of antimicrobials which could be incorporated into the composition according to the invention either alone or in combinations is shown in Table 1.

The concentrations used in the agar is preferably related to the S/R breakpoint for the particular drug, however, it will be within the capacity of a skilled person to determine the exact concentration needed for a particular purpose.

TABLE 1

List of antibiotics, IUPAC codes and concentration range for possible concentrations used in agar

| Antibiotic | Chemical name (IUPAC) | Range of concentrations covered Mg/l |
|---|---|---|
| Amikacin | 2S)-4-amino-N-[(2S,3S,4R,5S)-5-amino-2-[(2S,3R,4S,5S,6R)-4-amino-3,5-dihydroxy-6-(hydroxymethyl)oxan-2-yl]oxy-4-[(2R,3R,4S,5R,6R)-6-(aminomethyl)-3,4,5-trihydroxy-oxan-2-yl]oxy-3-hydroxy-cyclohexyl]-2-hydroxy-butanamide | 2-128 |
| Amoxicillin | 7-[2-amino-2-(4-hydroxyphenyl)-acetyl]amino-3,3-dimethyl-6-oxo-2-thia-5-azabicyclo[3.2.0]heptane-4-carboxylic acid | 0.1-32 |
| Amoxicillin-clavulanic acid | Amoxicillin: 7-[2-amino-2-(4-hydroxyphenyl)-acetyl]amino-3,3-dimethyl-6-oxo-2-thia-5-azabicyclo[3.2.0]heptane-4-carboxylic acid -Clavulanic acid: (2R,5R,Z)-3-(2-hydroxyethylidene)-7-oxo-4-oxa-1-aza-bicyclo[3.2.0]heptane-2-carboxylic acid | 0.1-32 |
| Amphothericin-B | (1R-1R*,3S*,5R*,6R*,9R*,11R*,15S*,16R*,17R*,18S*,19E,21E,23E,25E,27E,29E,31E,33R*,35S*,36R*,37S*))-33-((3-Amino-3,6-dideoxy-beta-D-mannopyranosyl)oxy)-1,3,5,6,9,11,17,37-octahydroxy-15,16,18-trimethyl-13-oxo-14,39-dioxabicyclo(33.3.1)nonatriaconta-19,21,23,25,27,29,31-heptaene-36-carboxylic acid | 0.1-64 |
| Ampicillin | 7-(2-amino-2-phenyl-acetyl)amino-3,3-dimethyl-6-oxo-2-thia-5-azabicyclo[3.2.0]heptane-4-carboxylic acid | 0.1-32 |
| Ampicillin | 7-(2-amino-2-phenyl-acetyl)amino-3,3-dimethyl-6-oxo-2-thia-5-azabicyclo[3.2.0]heptane-4-carboxylic acid | 0.1-32 |
| Sulbactam | (2R,5R)-3,3-dimethyl-4,4,7-trioxo-4$\lambda^6$-thia-1-azabicyclo[3.2.0]heptane-2-carboxylic acid | |
| Apramycin | (2R,3R,4R,5S,6R)-5-amino-2-[((1R,2R,3R,4R,6R,8R)-8-amino-9[(1R,2S,3R,4R,6R)-4,6-diamino-2,3-dihydroxy-cyclohexyl]oxy-2-hydroxy-3-methylamino-5,10dioxabicyclo[4.4.0]dec-4-yl)oxy]-6-(hydroxymethyl)oxane-3,4-diol | 0.5-128 |
| Azithromycin | 9-deoxy-9a-aza-9a-methyl-9a- homoerythromycin A | 0.03-64 |
| Aztreonam | 3-[2-(2-azaniumyl-1,3-thiazol-4-yl)-2-(1-hydroxy-2-methyl-1-oxo-propan-2-yl)oxyimino-acetyl]amino-2-methyl-4-oxo-azetidine-1-sulfonate | 0.25-16 |
| Bacitracin | | 1-128 |
| Benzylpenicillin | 4-Thia-1-azabicyclo(3.2.0)heptane-2-carboxylic acid, 3,3-dimethyl-7-oxo-6-((phenylacetyl)amino)-(2S-(2alpha,5alpha,6beta))- | 0.03-256 |

TABLE 1-continued

List of antibiotics, IUPAC codes and concentration range for possible concentrations used in agar

| Antibiotic | Chemical name (IUPAC) | Range of concentrations covered Mg/l |
|---|---|---|
| Caspofungin | 1-[(4R,5S)-5-[(2-aminoethyl)amino]-N2-(10,12-dimethyl-1-oxotetradecyl)-4-hydroxy-L-ornithine]-5-[(3R)-3-hydroxy-L-ornithine] pneumocandin B0 | 0.1-64 |
| Cefaclor | 7-[(2-amino-2-phenyl-acetyl)amino]-3-chloro-8-oxo-5-thia-1-azabicyclo [4.2.0] oct-2-ene-2-carboxylic acid | 0.05-256 |
| Cefadroxil | 8-[2-amino-2-(4-hydroxyphenyl)-acetyl]amino-4-methyl-7-oxo-2-thia-6-azabicyclo [4.2.0] oct-4-ene-5-carboxylic acid | 1-256 |
| Cefalexin | 8-(2-amino-2-phenyl-acetyl)amino-4-methyl-7-oxo-2-thia-6-azabicyclo [4.2.0]oct-4-ene-5-carboxylic acid | 4-256 |
| Cefalothin | (6R,7R)-3-(acetoxymethyl)-8-oxo-7-(2-(thiophen-2-yl)acetamido)-5-thia-1-azabicyclo[4.2.0]oct-2-ene-2-carboxylic acid | 1-256 |
| Cefazolin | 3-[(5-methyl-1,3,4-thiadiazol-2-yl)sulfanylmethyl]-8-oxo-7-([2-(tetrazol-1-yl)acetyl]amino)-5-thia-1-azabicyclo[4.2.0] oct-2-ene-2-carboxylate | 2-32 |
| Cefdinir | 8-[2-(2-amino-1,3-thiazol-4-yl)-1-hydroxy-2-nitroso-ethenyl]amino-4-ethenyl-7-oxo-2-thia-6-azabicyclo[4.2.0]oct-4-ene-5-carboxylic acid | 0.1-128 |
| Cefepime | (6R,7R,Z)-7-(2-(2-aminothiazol-4-yl)-2-(methoxyimino)acetamido)-3-((1-methylpyrrolidinium-1-yl)methyl)-8-oxo-5-thia-1-azabicyclo[4.2.0]oct-2-ene-2-carboxylate | 0.1-16 |
| Cefixime | (6R,7R)-7-{[2-(2-amino-1,3-thiazol-4-yl)-2-(carboxy methoxyimino)acetyl]amino}-3-ethenyl-8-oxo-5-thia-1-azabicyclo[4.2.0]oct-2-ene-2-carboxylic acid | 0.01-256 |
| Cefmenoxime | (6R,7R)-7-{[(2E)-2-(2-amino-1,3-thiazol-4-yl)-2-methoxyimino-acetyl]amino}-3-[(1-methyltetrazol-5-yl)sulfanylmethyl]-8-oxo-5-thia-1-azabicyclo[4.2.0] oct-2-ene-2-carboxylic acid | 0.1-256 |
| Cefoperazone | (6R,7S)-7-{[2-[(4-ethyl-2,3-dioxo-iperazine-1-carbonyl)amino]-2-(4-hydroxyphenyl)acetyl]amino]-3-[(1-methyltetrazol-5-yl)sulfanylmethyl]-8-oxo-5-thia-1-azabicyclo[4.2.0]oct-2-ene-2-carboxylic acid | 0.1-520 |
| Cefoperazone | (6R,7S)-7-{[2-[(4-ethyl-2,3-dioxo-piperazine-1-carbonyl)amino]-2-(4-hydroxyphenyl)acetyl]amino]-3-[(1-methyltetrazol-5-yl)sulfanylmethyl]-8-oxo-5-thia-1-azabicyclo[4.2.0]oct-2-ene-2-carboxylic acid | 0.1-520 |
| Sulbactam | (2R,5R)-3,3-dimethyl-4,4,7-trioxo-4$\lambda^6$-thia-1-azabicyclo[3.2.0]heptane-2-carboxylic acid | |
| Cefotaxime | (6R,7R,Z)-3-(acetoxymethyl)-7-(2-(2-aminothiazol-4-yl)-2-(methoxyimino) acetamido)-8-oxo-5-thia-1-azabicyclo[4.2.0] oct-2-ene-2-carboxylic acid | 0.03-32 |
| Cefoxitin | (6S,7R)-4-(carbamoyloxymethyl)-7-methoxy-8-oxo-7-[(2-thiophen-2-ylacetyl)amino]-5-thia-1-zabicyclo[4.2.0]oct-2-ene-2-carboxylic acid | 4-64 |
| Cefpirome | 5H-Cyclopenta[b]pyridinium, 1-[[[(6R,7R)-7-[[(2Z)-2-(2-amino-4-thiazolyl)-2-(methoxyimino)acetyl]amino]-2-carboxy-8-oxo-5-thia-1-azabicyclo[4.2.0]oct-2-en-3-yl]methyl]-6,7-dihydro- | 0.01-256 |
| Cefpodoxime | (6R,7R)-7-{[(2Z)-2-(2-amino-1,3-thiazol-4-yl)-2-methoxyimino-acetyl]amino}-3-(methoxymethyl)-8-oxo-5-thia-1-azabicyclo[4.2.0]oct-2-ene-2-carboxylic acid | 0.05-16 |
| Cefpodoxime | 2R,5R,Z)-3-(2-hydroxyethylidene)-7-oxo-4-oxa-1-aza-bicyclo[3.2.0]heptane-2-carboxylic acid | 0.05-16 |
| clavulanic acid | (2R,5R,Z)-3-(2-hydroxyethylidene)-7-oxo-4-oxa-1-aza-bicyclo[3.2.0]heptane-2-carboxylic acid | |
| Cefpodoxime | (6R,7R)-7-{[(2Z)-2-(2-amino-1,3-thiazol-4-yl)-2-methoxyimino-acetyl]amino}-3-(methoxymethyl)-8-oxo-5-thia-1-azabicyclo[4.2.0]oct-2-ene-2-carboxylic acid | 0.05-16 |
| sulbactam | (2R,5R)-3,3-dimethyl-4,4,7-trioxo-4$\lambda^6$-thia-1-azabicyclo[3.2.0]heptane-2-carboxylic acid | |
| Cefprozil | 8-[2-amino-2-(4-hydroxyphenyl)-acetyl] amino-7-oxo-4-prop-1-enyl-2-thia-6-azabicyclo [4.2.0]oct-4-ene-5-carboxylic acid | 1-512 |
| Cefquinome | Pharmacotherapeutic group: Cephalosporins and related substancesATCvet code: QJ51DA92 | 1-512 |
| Ceftazidime | (6R,7R,Z)-7-(2-(2-aminothiazol-4-yl)-2-(2-carboxypropan-2-yloxyimino)acetamido)-8-oxo-3-pyridinium-1-ylmethyl)-5-thia-1-aza-bicyclo[4.2.0] oct-2-ene-2-carboxylate | 0.1-32 |
| Ceftibutin | (+)-(6R,7R)-7-[(Z)-2-(2-Amino-4-thiazolyl)-4-carboxycroton-amido]-8-oxo-5-thia-1-azabicyclo[4.2.0]oct-2-ene-carboxylic acid | 0.5-32 |
| Ceftiofur | 6r-[6a,7b(z)]]-7-[[(2-amino-4-thiazolyl)(methoxyimino)acetyl]amino]-3-[[2-furanylcarbonyl) thio] methyl]-8-oxo-5-thia-1-azabicyclo [4.2.0] oct-2-ene-2-carboxylic acid; (6R-7R)-7-[[2-amino-4-thiazolyl)-z- | 0.1-128 |

TABLE 1-continued

List of antibiotics, IUPAC codes and concentration range for possible concentrations used in agar

| Antibiotic | Chemical name (IUPAC) | Range of concentrations covered Mg/l |
|---|---|---|
| Ceftobiprole | methoxyimino)acetyl]amino]-3-[[(2-furanylcarbonyl) thio] methyl]-8-oxo-5-thia-1-azabicyclo [4.2.0]oct-2-ene-carboxylic acid Ceftobiprole medocaril | 0.03-512 |
| Ceftriaxon | (6R,7R,Z)-7-(2-(2-aminothiazol-4-yl)-2-(methoxyimino)acetamido)-3-((6-hydroxy-2-methyl-5-oxo-2,5-dihydro-1,2,4-triazin-3-ylthio)methyl)-8-oxo-5-thia-1-aza-bicyclo[4.2.0]oct-2-ene-2-carboxylic acid | 0.01-16 |
| Cefuroxime | 4-(carbamoyloxymethyl)-8-[2-(2-furyl)-2-methoxyimino-acetyl]amino-7-oxo-2-thia-6-azabicyclo[4.2.0]oct-4-ene-5-carboxylic acid | 0.1-64 |
| Chloramphenicole | 2,2-dichlor-N-[(aR,bR)-b-hydroxy-a-hydroxymethyl-4-nitrophenethyl] acetamide | 0.5-128 |
| Florfenicole |  | 2-128 |
| Ciprofloxacin | 1-cyclopropyl-6-fluoro-4-oxo-7-piperazin-1-yl-quinoline-3-carboxylic acid | 0.01-32 |
| Clarithromycin | 6-(4-dimethylamino-3-hydroxy-6-methyl-etrahydropyran-2-yl) oxy-14-ethyl-12,13-dihydroxy-4-(5-hydroxy-4-methoxy-4,6-dimethyl-tetrahydropyran-2-yl) oxy-7-methoxy-3,5,7,9,11,13-hexamethyl-1-oxacyclotetradecane-2,10-dione | 0.03-64 |
| Clinafloxacin | 3-Quinolinecarboxylic acid, 7-(3-amino-1-pyrrolidinyl)-8-chloro-1-cyclopropyl-6-fluoro-1,4-dihydro-4-oxo- | 0.01-64 |
| Clindamycin | (2S,4R)-N-((1R)-2-chloro-1-((3R,4R,5S,6R)-3,4,5-trihydroxy-6-(methylthio)-tetrahydro-2H-pyran-2-yl)propyl)-1-methyl-4-propylpyrrolidine-2-carboxamide | 0.05-32 |
| Cloxacillin | (2S,5R,6R)-6-{[3-(2-chlorophenyl)-5-methyl-oxazole-4-carbonyl]amino}-3,3-dimethyl-7-oxo-4-thia-1-azabicyclo[3.2.0]heptane-2-carboxylic acid | 0.5-128 |
| Colistin | colistin sulfate and colistimethate sodium (colistin methanesulphonate sodium, colistin sulfomethate sodium | 0.5-16 |
| Cotrimoxazol (Trimthoprim/sulpha-meth-oxazole) | Trimethoprim: 5-(3,4,5-trimethoxybenzyl)pyrimidine-2,4-diamine/Sulphamethoxazole: 4-amino-N-(5-methylisoxazol-3-yl)-benzenesulfonamide | 1-128 |
| Dalbavancin | Semi-synthetic lipopeptide; 5,31-dichloro-38-de(methoxycarbonyl)-7-demethyl-19-deoxy-56-O-[2-deoxy-2-[(10-methyl-1-oxoundecyl)amino]-b-D-glucopyranuronosyl]-38-[[[3-(dimethylamino)propyl]amino]carbonyl]-42-O-a-D-mannopyranosyl-N15-methyl-Ristomycin A aglycone | 0.05-16 |
| Dalfopristin/ Quinopristin | quinupristine N-[(6R,9S,10R,13S,15aS,18R,22S,24aS)-22-[p-(dimethylamino)benzyl]-6-ethyldocosahydro-10,23-dimethyl-5,8,12,15,17,21,24-heptaoxo-13-phenyl-18-[[''(3S)-3-quinuclidinylthio]methyl]-12H-pyrido[2,1-f]pyrrolo-[2,1-l][1,4,7,10,13,16] oxapentaazacyclononadecin-9-yl]-3-hydroxypicolinamide dalfopristin (3R,4R,5E,10E,12E,14S,26R,26aS)-26-[[2-(diethylamino)ethyl]sulfonyl]-8,9,14,15,24,25,26,26a-octahydro-14-hydroxy-3-isopropyl-4,12-dimethyl-3H-21,18-nitrilo-1H,22H-pyrrolo[2,1-c][1,8,4,19]dioxadiazacyclotetracosine-1,7,16,22(4H,17H)-tetrone | 0.25-256 |
| Daptomycin | N-decanoyl-L-tryptophyl-L-asparaginyl-L-aspartyl-L-threonylglycyl-L-ornithyl-L-aspartyl-D-alanyl-L-aspartylglycyl-D-seryl-threo-3-methyl-L-glutamyl-3-anthraniloyl-L-alanine[egr]$_1$-lactone | 0.1-32 |
| Dibekacin | D-Streptamine, O-3-amino-3-deoxy-alpha-D-glucopyranosyl-(1-6)-O-(2,6-diamino-2,3,4,6-tetradeoxy-alpha-D-erythro-hexopyranosyl-(1-4))-2-deoxy | 1-128 |
| Dicloxacillin | (2S,5R,6R)-6-{[3-(2,6-dichlorophenyl)-5-methyl-oxazole-4-carbonyl]amino}-3,3-dimethyl-7-oxo-4-thia-1-azabicyclo[3.2.0]heptane-2-carboxylic acid | 0.2-128 |
| Doripenem | 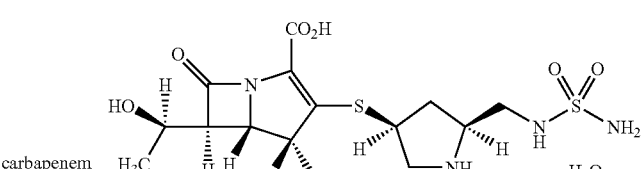 | 0.01-256 |
| Doxycycline | (2-amino-hydroxy-methylidene)-4-dimethylamino-5,10,11,12a-tetrahydroxy-6-methyl-4a,5,5a,6-tetrahydro-4H-tetracene-1,3,12-trione | 0.1-16 |
| Enrofloxacin | 1-Cyclopropyl-7-(4-ethylpiperazin-1-yl)-6-fluor-4-oxo-1,4-dihydrochinolin-3-carboxylic acid | 0.01-32 |

TABLE 1-continued

List of antibiotics, IUPAC codes and concentration range for possible concentrations used in agar

| Antibiotic | Chemical name (IUPAC) | Range of concentrations covered Mg/l |
|---|---|---|
| Ertapenem | 3-[5-[(3-carboxyphenyl) carbamoyl]pyrrolidin-3-yl] sulfanyl-7-(1-hydroxyethyl)-2-methyl-6-oxo-5-azabicyclo[3.2.0] hept-3-ene-4-carboxylic acid | 0.01-128 |
| Erythromycin | 6-(4-dimethylamino-3-hydroxy-6-methyl-oxan-2-yl)oxy-14-ethyl-7,12,13-trihydroxy-4-(5-hydroxy-4-methoxy-4,6-dimethyl-oxan-2-yl)oxy-3,5,7,9,11,13-hexamethyl-1-oxacyclotetradecane-2,10-dione | 0.03-64 |
| Flucloxacillin | 6-((S)-3-(2-chloro-6-fluorophenyl)-5-methylisoxazole-4-carboxamido)-3,3-dimethyl-7-oxo-4-thia-1-azabicyclo[3.2.0]heptane-2-carboxylic acid | 0.5-128 |
| Fluconazol | 2-(2,4-difluorophenyl)-1,3-bis(1H-1,2,4-triazol-1-yl)propan-2-ol | 0.25-512 |
| Flucytosin | 4-amino-5-fluoropyrimidin-2(1H)-one | 1-512 |
| Fosfomycin | [(2R,3S)-3-methyloxiran-2-yl]phosphonic acid | 1-64 |
| Fusidic acid | 2-(16-acetyloxy-3,11-dihydroxy-4,8,10,14-tetramethyl-2,3,4,5,6,7,9,11,12,13,15,16-dodecahydro-1H-cyclopenta [a]phenanthren-17-ylidene)-6-methyl-hept-5-enoic acid | 0.05-16 |
| Garenoxacin | fluoroquinolone | 0.01-32 |
| Gatifloxacin | 1-cyclopropyl-6-fluoro-8-methoxy-7-(3-methylpiperazin-1-yl)-4-oxo-quinoline-3-carboxylic aci | 0.01-32 |
| Gemifloxacin | 7-[(4Z)-3-(aminomethyl)-4-methoxyimino-pyrrolidin-1-yl]-1-cyclopropyl-6-fluoro-4-oxo-1,8-naphthyridine-3-carboxylic acid | 0.01-32 |
| Gentamicin | 2-[4,6-diamino-3-[3-amino-6-(1-methylaminoethyl) tetrahydropyran-2-yl] oxy-2-hydroxy-cyclohexoxy]-5-methyl-4-methylamino-tetrahydropyran-3,5-diol | 0.5-128 |
| Imipenem | (5R,6S)-3-[2-(aminomethylideneamino)ethylsulfanyl]-6-(1-hydroxyethyl)-7-oxo-1-azabicyclo[3.2.0]hept-2-ene-2-carboxylic acid | 0.01-128 |
| Itraconazole | 4-[4-[4-[ [2-(2,4-dichlorophenyl)-2-(1H-1,2,4-triazol-1-ylmethyl)-1,3-dioxolan-4-yl]methoxy]phenyl] piperazine-1-yl]phenyl]-2-(1-methylpropyl)-2,4-dihydro-1,2,4-triazol-3-one | 0.1-256 |
| Kanamycin | 2-(aminomethyl)-6-[4,6-diamino-3-[4-amino-3,5-dihydroxy-6-(hydroxymethyl) tetrahydropyran-2-yl] oxy-2-hydroxy-cyclohexoxy]-tetrahydropyran-3,4,5-triol | 2-256 |
| Ketoconazole | 1-[4-[4-[[(2S,4R)-2-(2,4-dichlorophenyl)-2-(imidazol-1-ylmethyl)-1,3-dioxolan-4-yl]methoxy] phenyl]piperazin-1-yl]ethanone | 0.03-512 |
| Levofloxacin | (−)-(S)-9-fluoro-2,3-dihydro-3-methyl-10-(4-methyl-1-piperazinyl)-7-oxo-7H-pyrido [1,2,3-de]-1,4-benzoxazine-6-carboxylic acid | 0.01-32 |
| Lincomycin | 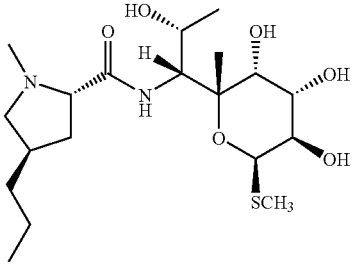 [SMILES: CCC[C@@H]1C[C@@H](C(=O)N[C@H]([C@@H](C)O)[C@@]2(C)O[C@H](SC)[C@H](O)[C@@H](O)[C@H]2O)N(C)C1] | 1-32 |
| Linezolid | N-[[3-(3-fluoro-4-morpholinophenyl)-2-oxooxazolidin-5-yl]methyl]acetamide | 1-32 |
| Loracarbef | 8-(2-amino-2-phenyl-acetyl)amino-4-chloro-7-oxo-6-azabicyclo[4.2.0] oct-4-ene-5-carboxylic acid | 0.1-128 |
| Mecillnam (amdinocillin) | 6-Amidinopenicillanic acid derivatives; amdinocillin: 46-[[(hexahydro-1H-azepin-1-yl)methylene]amino]-3,3-dimethyl-7-oxo-, (2S,5R,6R)--Thia-1-azabicyclo[3.2.0]heptane-2-carboxylic acid | 0.25-254 |
| Meropenim | 3-[5-(dimethylcarbamoyl) pyrrolidin-2-yl] sulfanyl-6-(1-hydroxyethyl)-4-methyl-7-oxo-1-azabicyclo[3.2.0] hept-2-ene-2-carboxylic acid | 0.03-256 |
| Metronidazole | 2-(2-methyl-5-nitro-1H-imidazol-1-yl)ethanol | 1-512 |
| Mezlocillin | (2S,5R,6R)-3,3-dimethyl-6-[[(2R)-2-[(3-methylsulfonyl-2-oxo-imidazolidine-1-carbonyl)amino]-2-phenyl-acetyl]amino]-7-oxo-4-thia-1-azabicyclo[3.2.0]heptane-2-carboxylic acid | 0.5-512 |
| Mezlocillin-sulbactam | Mezlocillin: (2S,5R,6R)-3,3-dimethyl-6-[[(2R)-2-[(3-methylsulfonyl-2-oxo-imidazolidine-1-carbonyl)amino]-2-phenyl-acetyl]amino]-7-oxo-4-thia-1-azabicyclo[3.2.0]heptane-2-carboxylic acid Sulbactam: (2R,5R)-3,3-dimethyl-4,4,7-trioxo-4$\lambda^6$-thia-1-azabicyclo[3.2.0]heptane-2-carboxylic acid | 0.5-512 |

TABLE 1-continued

List of antibiotics, IUPAC codes and concentration range for possible concentrations used in agar

| Antibiotic | Chemical name (IUPAC) | Range of concentrations covered Mg/l |
|---|---|---|
| Minocycline | 2-(amino-hydroxy-methylidene)-4,7-bis(dimethylamino)-10,11,12a-trihydroxy-4a,5,5a,6-tetrahydro-4H-tetracene-1,3,12-trione (synonym 7-Dimethylamino-6-demethyl-6-deoxytetracycline) | 0.1-256 |
| Moxifloxacin,, | 1-cyclopropyl-7-[(1S,6S)-2,8-diazabicyclo[4.3.0]non-8-yl]-6-fluoro-8-methoxy-4-oxo-quinoline-3-carboxylic acid | 0.01-32 |
| Mupirocin | pseudomonic acid A; 9-[[(2Z)-3-methyl-1-oxo-4-[(2S,3R,4R,5S)-tetrahydro-3,4-dihydroxy-5-[[(2S,3S)-3-[(1S,2S)-2-hydroxy-1-methylpropyl]-2-oxiranyl]methyl]-2H-pyran-2-yl]-2-buten-1-yl]oxy]-Nonanoic acid | 0.1-256 |
| Nalidixic acid | 1-ethyl-7-methyl-4-oxo-[1,8]naphthyridine-3-carboxylic acid | 4-1024 |
| Neomycin | $C_{23}H_{46}N_6O_{13}$ (MW 614.644 g/mol) | 0.5-256 |
| Netilmicin | $C_{21}H_{41}N_5O_7$ (MW 475.58 g/mol); O-3-deoxy-4-C-methyl-3-(methylamino)-b-L-arabinopyranosyl-(1->6)-O-[2,6-diamino-2,3,4,6-tetradeoxy-a-D-glycero-hex-4-enopyranosyl-(1->4)]-2-deoxy-N1-ethyl-D-Streptamine | 0.5-512 |
| Nitrofurantoin | 1-[(5-nitro-2-furyl)methylideneamino]imidazolidine-2,4-dione | 1-1028 |
| Norfloxacin | 1-ethyl-6-fluoro-4-oxo-7-piperazin-1-yl-1H-quinoline-3-carboxylic acid | 0.5-128 |
| Ofloxacin | (+/-)-9-fluoro-2,3-dihydro-3-methyl-10-(4-methyl-1-piperazinyl)-7-oxo-7H-pyrido [1,2,3-de]-1,4-benzoxazine-6-carboxylic acid | 0.01-32 |
| Oxacillin | (2R,5R,6S)-3,3-dimethyl-6-[(5-methyl-3-phenyl-1,2-oxazole-4-carbonyl)amino]-7-oxo-4-thia-1-azabicyclo[3.2.0]heptane-2-carboxylic acid | 0.25-128 |
| Pefloxacin | 1-ethyl-6-fluoro-7-(4-methylpiperazin-1-yl)-4-oxo-quinoline-3-carboxylic acid | 0.01-32 |
| Penicillin V | Phenoxymethylpenicillin | 0.1-256 |
| Piperacillin | (2S,5R,6R)-6-{[(2R)-2-[(4-ethyl-2,3-dioxo-piperazine-1-carbonyl)amino]-2-phenyl-acetyl]amino}-3,3-dimethyl-7-oxo-4-thia-1-azabicyclo[3.2.0]heptane-2-carboxylic acid | 2-1024 |
| Piperacillin-sulbactam | Piperacillin: (2S,5R,6R)-6-{[(2R)-2-[(4-ethyl-2,3-dioxo-piperazine-1-carbonyl)amino]-2-phenyl-acetyl]amino}-3,3-dimethyl-7-oxo-4-thia-1-azabicyclo[3.2.0]heptane-2-carboxylic acid Sulbactam: (2R,5R)-3,3-dimethyl-4,4,7-trioxo-4$\lambda^6$-thia-1-azabicyclo[3.2.0]heptane-2-carboxylic acid | 2-1024 |
| Piperacillin-tazobactam | Piperacillin: as above; Tazobactam: (2S,3S,5R)-3-methyl-4,4,7-trioxo-3-(triazol-1-ylmethyl)-4$1^{\wedge}${6}-thia-1-azabicyclo[3.2.0] heptane-2-carboxylic acid | 2-1024 |
| Rifampicin | 5,6,9,17,19,21-Hexahydroxy-23-methoxy-2,4,12,16,18,20,22-heptamethyl-8-[N-(4-methyl-1-piperazinyl)formimidoyl]-2,7-(epoxypentadeca[1,11,13]trienimino)-naphtho[2,1-b]furan-1,11(2H)-dione 21-acetate | 0.005-128 |
| Roxythromycin | Erythromycin-[O-[(2-methoxyethoxy)-methyl]oxime] | 0.03-64 |
| Sparfloxacin | 5-amino-1-cyclopropyl-7-[(3R,5S)3,5-dimethylpiperazin-1-yl]-6,8-difluoro-4-oxo-quinoline-3-carboxylic acid | 0.01-128 |
| Spectinomycin | (2R,4aR,5aR,6S,7S,8R,9S,9aR,10aS)-4a,7,9-trihydroxy-2-methyl-6,8-bis(methylamino) decahydro-4H-pyrano[2,3-b][1,4]benzodioxin-4-one | 32-512 |
| Spiramycin | $C_{43}H_{74}N_2O_{14}$, (MW 843.053 g/mol) | 0.05-8 |
| Streptomycin | 5-(2,4-diguanidino-3,5,6-trihydroxy-cyclohexoxy)-4-[4,5-dihydroxy-6-(hydroxymethyl)-3-methylamino-tetrahydropyran-2-yl] oxy-3-hydroxy-2-methyl-tetrahydrofuran-3-carbaldehyde | 2-1024 |
| Sulbactam | (2R,5R)-3,3-dimethyl-4,4,7-trioxo-4$\lambda^6$-thia-1-azabicyclo[3.2.0]heptane-2-carboxylic acid | 2-1024 |
| Sulfamethoxazole | 4-amino-N-(5-methylisoxazol-3-yl)-benzenesulfonamide | 16-2050 |
| Teicoplanin | Glycopeptide - no IUPAC-code | 0.05-128 |
| Telavancin | Lipopeptide - N3"-[2-(decylamino)ethyl]-29-[[(phosphonomethyl)amino]methyl]-Vancomycin | 0.25-128 |
| Telithromycin | (1S,2R,5R,7R,8R,9S,11R,13R,14R)-8-[(2S,3R,4S,6R)-4-dimethylamino-3-hydroxy-6-methyl-oxan-2-yl]oxy-2-ethyl-9-methoxy-1,5,7,9,11,13-hexamethyl-15-[4-(4-pyridin-3-ylimidazol-1-yl)butyl]-3,17-dioxa-15-azabicyclo[12.3.0]heptadecane-4,6,12,16-tetrone | 0.01-64 |
| Temocillin | (2S,5R,6S)-6-[(Carboxy-3-thienylacetyl)amino]-6-methoxy-3,3-dimethyl-7-oxo-4-thia-1-azabicyclo[3.2.0] heptane-2-carboxylic acid, | 0.1-1024 |
| Tetracyklin | 2-(amino-hydroxy-methylidene)-4-dimethylamino-6,10,11,12a-tetrahydroxy-6-methyl-4,4a,5,5a-tetrahydrotetracene 1,3,12-trione OR 4-(dimethylamino)-1,4,4a,5,5a,6,11,12a-octahydro-3,6,10,12,12a-pentahydroxy-1,11dioxo-naphthacene-2carboxamide | 0.1-32 |
| Ticarcillin | 2S,5R,6R)-6-[[(2R)-2-carboxy-2-thiophen-3-yl-acetyl]amino]-3,3-dimethyl-7-oxo-4-thia-1-azabicyclo[3.2.0]heptane-2-carboxylic acid | 2-512 |

TABLE 1-continued

List of antibiotics, IUPAC codes and concentration range for possible concentrations used in agar

| Antibiotic | Chemical name (IUPAC) | Range of concentrations covered Mg/l |
|---|---|---|
| Ticarcillin-clavulanic acid | Ticarcillin: 2S,5R,6R)-6-[[(2R)-2-carboxy-2-thiophen-3-yl-acetyl]amino]-3,3-dimethyl-7-oxo-4-thia-1-azabicyclo[3.2.0]heptane-2-carboxylic acid- Clavulanic acid: (2R,5R,Z)-3-(2-hydroxyethylidene)-7-oxo-4-oxa-1-aza-bicyclo[3.2.0]heptane-2-carboxylic acid | 2-512 |
| Tigecycline | N-[(5aR,6aS,7S,9Z,10aS)-9-(amino-hydroxy-methylidene)-4,7-bis(dimethylamino)-1,10a,12-trihydroxy-8,10,11-trioxo-5a,6,6a,7-tetrahydro-5H-tetracen-2-yl]-2-(tert-butylamino)acetamide | 0.1-256 |
| Tobramycin | 4-amino-2-[4,6-diamino-3-[3-amino-6-(aminomethyl)-5-hydroxy-etrahydropyran-2-yl]oxy-2-hydroxy-cyclohexoxy]-6-(hydroxymethyl) tetrahydropyran-3,5-diol | 0.5-128 |
| Trimethoprim | S-(3,4,5-trimethoxybenzyl)pyrimidine-2,4-diamine | 0.25-64 |
| Trovafloxacin | 7-(6-amino-3-azabicyclo[3.1.0]hex-3-yl)-1-(2,4-difluorophenyl)-6-fluoro-4-oxo-[1,8] naphthyridine-3-carboxylic acid | 0.1-32 |
| Tylosin | macrolide | 0.1-32 |
| Vancomycin | $C_{66}H_{75}Cl_2N_9O_{24}$ | 0.5-1024 |
| Virginiamycin | $C_{71}H_{84}N_{10}O_{17}$ | 0.25-256 |
| Voriconazole | 2-(2,4-difluorophenyl)-3-(5-fluoropyrimidin-4-yl)-1-(1H-1,2,4-triazol-1-yl) butan-2-ol | 0.004-128 |

The prevalence of antibiotic resistance has been and is continuing to increase in all bacteria including *E. coli*, and it is now becoming increasingly necessary to combine urine culture with a susceptibility test even in primary care.

In a recent study surveying resistance rates in *E. coli* from North America (USA and Canada)[8], of the 1142 *E. coli* collected, 75.5% (862) were collected from the USA and 280 (24.5%) were from Canada. Overall, resistance to ampicillin was 37.7%, followed by SMX/TMP (21.3%), nitrofurantoin (1.1%), ciprofloxacin (5.5%) and levofloxacin (5.1%). This study reported higher rates of antibiotic resistance in US versus Canadian outpatient urinary isolates of *E. coli* and demonstrated the continuing evolution of resistance to antimicrobial agents. In a European survey from 2002-3, the Eco-Sens study[9], antibiotic resistance rates were determined in *E. coli* from a range of European countries. The results are shown in table 2.

As can be deducted from these data, the resistance rates for commonly used antibiotics such as ampicillin, sulfonamides and trimethoprim are now so high (i.e. 15-45%), that these drugs cannot be used empirically without a susceptibility test. The use of fluoroquinolones, which are effective broad-spectrum drugs in some countries still covering most urinary pathogens, is directly related to development of resistance, which on even short-term scale is problematic due to the importance of these drugs for treating serious infections in hospitals. Since the resistance rates vary between geographic areas different antimicrobials may be preferred depending on the purpose for which the composition according to the invention is used.

In a presently preferred embodiment compositions according to the invention comprises one or more antimicrobials, wherein the antimicrobial/at least one of the antimicrobials is selected from the group consisting of: aminoglycosides, pip-

TABLE 2

Antimicrobial resistance of *E. coli* in European countries in the Eco-Sens study[9]

| Country | n | Antimicrobial agent[a] (resistance in percent) | | | | | | | | | | | |
|---|---|---|---|---|---|---|---|---|---|---|---|---|---|
| | | AMP | AMC | MEC | CFR | TMP | SUL | SXT | NAL | CIP | NIT | FOF | GEN |
| Austria | 126 | 17.5 | 2.4 | 1.6 | 0.8 | 9.5 | 25.4 | 9.5 | 2.4 | 0 | 0.8 | 0 | 0.8 |
| Belgium | 137 | 30.7 | 2.9 | 1.5 | 0.7 | 13.9 | 32.8 | 14.6 | 6.6 | 2.9 | 0.7 | 0.7 | 0.7 |
| Canada | 166 | 29.5 | 3.6 | 1.2 | 1.8 | 10.8 | 25.3 | 12.0 | 0.6 | 0 | 1.2 | 0.6 | 0.6 |
| Denmark | 85 | 22.4 | 1.2 | 1.2 | 1.2 | 10.6 | 21.2 | 8.2 | 3.5 | 0 | 1.2 | 1.2 | 0 |
| Finland | 182 | 19.8 | 4.9 | 0.5 | 1.6 | 5.5 | 15.4 | 4.9 | 1.6 | 0.5 | 0.5 | 1.1 | 0.5 |
| France | 199 | 27.6 | 1.5 | 1.5 | 1.0 | 15.6 | 31.7 | 15.1 | 3.5 | 2.0 | 1.0 | 1.0 | 0 |
| Germany | 138 | 29.0 | 2.2 | 2.2 | 1.4 | 22.5 | 34.8 | 21.0 | 3.6 | 2.2 | 0.7 | 0 | 0.7 |
| Greece | 132 | 22.0 | 0.8 | 0.8 | 3.0 | 13.6 | 19.7 | 11.4 | 6.8 | 1.5 | 3.0 | 1.5 | 0.8 |
| Ireland | 154 | 44.8 | 5.8 | 0.6 | 0.6 | 22.1 | 40.3 | 20.8 | 1.9 | 0 | 0 | 1.3 | 0.6 |
| Luxembourg | 24 | 41.7 | 0 | 0 | 0 | 16.7 | 25.0 | 16.7 | 8.3 | 4.2 | 4.2 | 0 | 0 |
| The Netherlands | 195 | 28.7 | 2.6 | 1.5 | 4.6 | 12.3 | 25.6 | 10.3 | 5.1 | 2.1 | 1.0 | 0.5 | 0.5 |
| Norway | 168 | 23.8 | 3.6 | 0 | 2.4 | 13.1 | 25.0 | 11.3 | 1.2 | 0 | 0 | 1.2 | 0 |
| Portugal | 86 | 45.3 | 9.3 | 2.3 | 2.3 | 26.7 | 44.2 | 26.7 | 11.6 | 5.8 | 5.8 | 0 | 3.5 |
| Spain | 191 | 53.9 | 4.2 | 1.0 | 3.1 | 25.1 | 48.7 | 25.7 | 26.7 | 14.7 | 4.2 | 0.5 | 4.7 |
| Sweden | 193 | 15.5 | 5.7 | 1.6 | 5.2 | 8.8 | 16.6 | 8.3 | 2.6 | 0 | 0 | 0.5 | 0 |
| Switzerland | 122 | 27.0 | 2.5 | 0 | 0.8 | 18.9 | 31.1 | 18.9 | 6.6 | 2.5 | 0.8 | 0.8 | 3.3 |
| United Kingdom | 180 | 37.2 | 2.8 | 1.7 | 1.7 | 13.3 | 31.7 | 12.2 | 2.2 | 0.6 | 0 | 0 | 0 |
| Total | 2478 | 29.8 | 3.4 | 1.2 | 2.1 | 14.8 | 29.1 | 14.1 | 5.4 | 2.3 | 1.2 | 0.7 | 1.0 |

[a]AMP, ampicillin; AMC, co-amoxiclav; MEC, mecillinam; CFR, cefadroxil; TMP, trimethoprim; SUL, sulfamethoxazole; SXT, trimethoprim/sulfamethoxazole; NAL, nalidixic acid; CIP, ciprofloxacin; NIT, nitrofurantoin; FOF, fosfomycin; GEN, gentamicin.

eracillin/tazobactam, carbapenems, cephalosporins, glycopeptides, lipopeptides and antimicrobial peptides (e.g. polymycin or colistin) and combinations of these.

In an equally preferred embodiment, compositions according to the invention are developed for use in diagnosing urinary tract infections in Denmark and the Scandinavian countries. In these compositions the antimicrobial or antimicrobials are preferably selected from the group consisting of: Ampicillin/amoxicillin, Sulfonamide, Trimethoprim, Nitrofurantoin, Mecillinam, and Ciprofloxacin (or other fluoroquinolone), and combinations of these.

For the same purpose it may be preferred that the antimicrobial is selected from the group consisting of: trimethoprim, sulfamethizole, ampicillin, nitrofurantoin and mecillinam (amdinocillin) and combinations of these.

For similar reason compositions have been developed for use in UTI diagnostics in Europe outside Scandinavia. In these compositions the antimicrobial or antimicrobials is/are preferably selected from the group consisting of: Amoxicillin, cluvulanic acid/ampicillin, sulbactam, Ciprofloxacin (or other fluoroquinolone), Sulphamethoxazole, trimethoprim, Cefalexin/cefuroxime/cefadroxil (or other oral cephalosporin), Nitrofurantoin and Fosfomycin (fosfomycin-trometerole) and combinations of these.

For the purpose of diagnosing UTI in the United Stated it may be preferred that antimicrobial or antimicrobials is/are selected from the group consisting of: Amoxicillin, cluvulanic acid/ampicillin, sulbactam, Ciprofloxacin (or other fluoroquinolone), Sulphamethoxazole, trimethoprim, Cefalexin/cefuroxime/cefadroxil/cefaclor (or other oral cephalosporin), Nitrofurantoin and Fosfomycin (fosfomycin-trometerole) and combinations of these.

It is to be understood in particular that amoxicillin may be included either alone or in combination with cluvulanic acid. Similarly, ampicillin may be included alone or in combination with sulbactam, and Sulphamethoxazole amy be used alone or in combination with trimethoprim.

For purposes other than diagnosing UTIs the antimicrobial or antimicrobials may also be selected from the group consisting of: Amoxicillin/clavulanic acid (or sulbactam), Phenoxymethyl-penicillin, Cephalosporin (e.g. cefuroxime axetil, cefalexin), Ciprofloxacin, levofloxacin, ofloxacin, fleroxacin, Sulphametoxazole and trimethoprim (optionally in combination as used for oral treatment), Tetracyclin (doxycycline or any other tetracyclin group), Chloramphenicol, Fosfomycin, Macrolide/clindamycin and Rifampicin, and combinations of these.

If the test would be used in a hospital laboratory, antibiotics for intravenous use might be considered also, including antimicrobials selected from the group consisting of: Aminoglycosides, Cephalosporins (cefotaxime, ceftazidime, cefepime, cefpodoxime, ceftriaxone and others), Piperacillin/tazobactam, Carbapenems, cephalosporins, Glycopeptides, Lipopeptides, Linezolid and antimicrobial peptides (e.g. polymycin or colistin) and combination of these.

Important Additives to the Selective Medium

Sulfa inhibitors and Metal ions: Variation in Mg and Ca, will affect results of aminoglycoside and tetracycline tests with *Ps. aeruginosa*. Excess zinc ions may reduce zone sizes of carbapenems. Excessive cation content will reduce antibiotic activity, whereas low cation content may result in enhanced activity Ca and Mg should be available in the medium in the form of soluble salts.

The thymidine content of the medium affects testing of trimethoprim and methicillin-resistant staphylococci. Most agar media contain small amounts of sulphonamide and trimethoprim antagonists that may affect the results of susceptibility testing (especially if blood is not added) with low antibiotic content in the medium. Susceptibility test media should contain less than 0.03 mg/l thymidine, otherwise small colonies are seen on the trimethoprim agar. If the medium contains slightly more thymidine than recommended, it is possible to reduce the concentration by adding thymidine-phosphorylase: 0.025 to 0.1 IU enzyme/ml medium or 5% haemolysed horse blood, which contains the same enzyme.

Prior to adding the antibiotic to the semi-solid media it may be an advantage to dissolve the antibiotic.

In particular solvents used to dissolve the antimicrobial agent(s) may include one or more of the following:

Water
Physiological saline 0.85%
Phosphate buffer, pH 6.0, 0.1 mol/L
Phosphate buffer, pH 8.0, 0.1 mol/L
Phosphate buffer, pH 7.2, 0.01 mol/L
Saturated solution sodium bicarbonate
Aqueous sodium bicarbonate 0.1%
Ethanol 95%
Methanol
Glacial acetic acid
Dimethylformamide (DMF)
Dimethyl sulfoxide (DMSO)
DMSO 1/10 vol
DMSO plus glacial acetic acid
½ volume of water plus drops of 1 mol/L Sodium hydroxide
½ volume of water plus drops of 0.1 mol/L Sodium hydroxide
½ volume of water plus drops of 2.5 mol/L Sodium hydroxide
Hydrogen chloride acid 0.04 mol/L
Polysorbate-80 (0.002%) in water Stability of the antimicrobial in the semi-solid media may depend on the pH-value. The pH-value should preferably not exceed certain limits as this will influence the antimicrobial effect. The stability of Ampicillin and Mecillinam has been improved by adjusting the pH-value of the semi-solid media to 6.0.

According to the invention the two or more chromogenic substances present in the composition is preferably selected from the group consisting of: 5-Bromo-4-chloro-3-indolyl phosphate, 5-Bromo-6-chloro-3-indolyl phosphate p-toluidine, 3,3'-(3,3'-dimethoxy-4,4'-biphenylylene)-bis-2-(p-nitrophenyl)-5-phenyl-2H-tetrazolium chloride, 5-Bromo-4-chloro-3-indolyl-β-D-galactopyranoside, 5-Bromo-6-chloro-3-indolyl-β-D-galactopyranoside, 5-Bromo-3-indolyl-β-D-galactopyranoside, 6-Bromo-2-naphthyl-β-D-galactopyranoside, 6-Chloro-3-indolyl-β-D-galactopyranoside, 6-Bromo-3-indolyl-β-D-galactopyranoside, 1-Methyl-3-indolyl-β-D-galactopyranoside, o-Nitrophenyl-β-D-galactopyranoside, p-Nitrophenyl-β-D-galactopyranoside, 3,4-cyclohexenoesculetin-β-D-galactoside, 8-hydroxychinoline-β-D-galactoside, 5-Bromo-4-chloro-3-indolyl-α-D-galactopyranoside, 5-Bromo-4-chloro-3-indolyl-β-D-glucopyranoside, 5-Bromo-4-chloro-3-indolyl-β-D-glucuronide, 5-Bromo-6-chloro-3-indolyl-β-D-glucuronide, 8-hydroxyquinoline-β-D-glucuronide, 2,2'-Azino-bis(3-ethylbenzothiazoline-6-sulfonic acid), 4-Chloro-1-naphthol, 3,3'-Diaminobenzidine tetrahydrochloride, o-Phenylenediamine, 3,3',5,5'-Tetramethylbenzidine, 4-[2-(4-octanoyloxy-3,5-dimethoxyphenyl)-vinyl]-quinolinium-1-[(ropan-3-yl-carboxylic-acid)-bromide, 5-Bromo-6-chloro-3-indolyl-caprylate and 5-bromo-4-chloro-3-indoxy]-myo-inositol-1-phosphate and combinations of these.

As the skilled person will know, the components listed above are normally used in an amount of 0.001-1.0 g/l.

In table 3 below, these chromogenes are listed according to the enzyme for which they serve as substrate:

TABLE 3

| ENZYME | SUBSTRATE | CONCENTRATION | COLOR |
|---|---|---|---|
| Alkaline Phosphatase | 5-Bromo-4-chloro-3-indolyl phosphate | 0.001 to 1.0 g/l | Blue |
| | 5-Bromo-6-chloro-3-indolyl phosphate p-toluidine | 0.001 to 1.0 g/l | Red |
| | 3,3'-(3,3'-dimethoxy-4,4'-biphenylylene)-bis-2-(p-nitrophenyl)-5-phenyl-2H-tetrazolium chloride | 0.001 to 1.0 g/l | Red |
| β-galactosidase | 5-Bromo-4-chloro-3-indolyl-β-D-galactopyranoside | 0.001 to 1.0 g/l | Blue |
| | 5-Bromo-6-chloro-3-indolyl-β-D-galactopyranoside | 0.001 to 1.0 g/l | Magenta |
| | 5-Bromo-3-indolyl-β-D-galactopyranoside | 0.001 to 1.0 g/l | Blue |
| | 6-Bromo-2-naphthyl-β-D-galactopyranoside | 0.001 to 1.0 g/l | — |
| | 6-Chloro-3-indolyl-β-D-galactopyranoside | 0.001 to 1.0 g/l | Salmon |
| | 6-Bromo-3-indolyl-β-D-galactopyranoside | 0.001 to 1.0 g/l | — |
| | 1-Methyl-3-indolyl-β-D-galactopyranoside | 0.001 to 1.0 g/l | Green |
| | o-Nitrophenyl-β-D-galactopyranoside | 0.001 to 1.0 g/l | Yellow |
| | p-Nitrophenyl-β-D-galactopyranoside | 0.001 to 1.0 g/l | Yellow |
| | 3,4-cyclohexenoesculetin-β-D-galactoside | 0.001 to 1.0 g/l | Brown/Black |
| | 8-hydroxychinoline-β-D-galactoside | 0.001 to 1.0 g/l | — |
| α-galactosidase | 5-Bromo-4-chloro-3-indolyl-α-D-galactopyranoside | 0.001 to 1.0 g/l | Blue |
| β-glucosidase | 5-Bromo-4-chloro-3-indolyl-β-D-glucopyranoside | 0.001 to 1.0 g/l | Blue |
| β-glucuronidase | 5-Bromo-4-chloro-3-indolyl-β-D-glucuronide | 0.001 to 1.0 g/l | Blue |
| | 5-Bromo-6-chloro-3-indolyl-β-D-glucuronide | 0.001 to 1.0 g/l | Magenta |
| | 8-hydroxyquinoline-β-D-glucuronide | 0.001 to 1.0 g/l | Black |
| Peroxidase | 2,2'-Azino-bis(3-ethylbenzothiazoline-6-sulfonic acid) | 0.001 to 1.0 g/l | Green |
| | 4-Chloro-1-naphthol | 0.001 to 1.0 g/l | Blue |
| | 3,3'-Diaminobenzidine tetrahydrochloride | 0.001 to 1.0 g/l | Brown |
| | o-Phenylenediamine | 0.001 to 1.0 g/l | — |
| | 3,3',5,5'-Tetramethylbenzidine | 0.001 to 1.0 g/l | Blue |
| Esterase | 4-[2-(4-octanoyloxy-3,5-dimethoxyphenyl)-vinyl]-quinolinium-1-(propan-3-yl-carboxylic-acid)-bromide | 0.001 to 1.0 g/l | Burgundy |
| | 5-Bromo-6-chloro-3-indolyl-caprylate | 0.001 to 1.0 g/l | Magenta |
| Phosphatidylinositol phospholipase C | 5-bromo-4-chloro-3-indoxyl-myo-inositol-1-phosphate | 0.001 to 1.0 g/l | Blue |

For the purpose of detecting or diagnosing urinary tract infections at least one of said two or more chromogenic substance is preferably selected from the group consisting of: 5-Bromo-4-chloro-3-indolyl-β-D-galactopyranoside, 6-Chloro-3-indolyl-β-D-galactopyranoside, 5-Bromo-4-chloro-3-indolyl-β-D-glucopyranoside, 5-Bromo-4-chloro-3-indolyl-β-D-glucuronide, and 5-Bromo-6-chloro-3-indolyl-phosphate or combinations of these. It may be preferred that the composition comprises 2, 3, 4, or 5 chromogenic substances, all selected from this group.

The fluorogenic substance of the composition according to the invention may be selected from the group consisting of: 4-Methylumbelliferyl phosphate, 4-Methylumbelliferyl-β-D-galactopyranoside, 4-Methylumbelliferyl β-D-lactopyranoside and 4-Methylumbelliferyl b-D-glucuronide or combinations of these.

As described previously the semi-solid media may in a particular embodiment comprise tryptophan, such as L-tryptophan. L-tryptophan present in the semi-solid media will be degraded by bacteria expressing tryptophanase to indole, pyruvate and ammonia. Enterobacteria of the Proteus-Morganella-Providencia group form a pigment from L-tryptophan colouring the agar surrounding the colony reddish brown to brown. Bacteria belonging to the Proteus group: Proteus mirabilis, P. vulgaris, P. penneri and P. myxofaciens. Bacteria belonging to the Morganella group: Morganella morganii. Bacteria belonging to the Providencia group: Providencia rettgeri, P. stuartii, P. alcalifaciens, P. rustigianii and P. heimbachae. Proteus spp., Morganella spp. and Providencia spp. producing tryptophan deaminase will deaminate the amino acid L-Tryptophan to indolepyruvic acid and ammonia. Indolepyruvic acid, ferric ions and hydrazine compounds in the culture media produce reddish to brown colour in the media. Bacteria degrading L-tryptophan to indole can further be detected by addition of a paper disc to the lid of the petri dish. The disc prepared with Ehrlich-Bohme's reagent (Paradimethylaminobenzaldehyd dissolved in ethylalkohol/HCl) will give a red colour with indol vapour formed during incubation.

In a further embodiment the semi-solid media of the present invention may comprise on or more inducers which are substances that positively regulate the expression of one or more genes. Induction is common in metabolic pathways that result in the catabolism of a substance and the inducer is normally the substrate for the pathway. The effects of inducers can be critical to the function and sensitivity of many routine assays. Adding inducers to the medium can increase the coloration. Common inducers are shown in table 4 below:

TABLE 4

| Inducers | | |
|---|---|---|
| Enzyme | Inducers | Concentration |
| B-galactosidase | 4-Aminophenyl-β-D-galactopyranoside | 0.001 to 1.0 g/l |
| | Isopropyl-β-D-thiogalactopyranoside | |
| | 1-O-Methyl-β-D-galactopyranoside | |
| | Methyl-β-D-thiogalactopyranoside | |
| A-galactosidase | 1-O-Methyl-α-D-galactopyranoside | 0.001 to 1.0 g/l |
| B-glucosidase | Isopropyl-β-D-thioglucopyranoside | 0.001 to 1.0 g/l |
| | 1-O-Methyl-β-D-glucopyranoside | |
| B-glucuronidase | Isopropyl-β-D-thioglucuronic acid, sodium salt | 0.001 to 1.0 g/l |
| | 1-O-Methyl-β-D-glucuronic acid, sodium salt | |

As the skilled person will know, the components listed above are normally used in an amount of 0.001-1.0 g/l.

The composition according to the invention may comprise 3 or more chromogenic or fluorescent substrates, such as 4 or more chromogenic or fluorescent substrates, 5 or more, 6 or more, 7 or more, 8 or more, 9 or more or 10 or more chromogenic or fluorescent substrates. In particular the composition according to the invention may comprise 2, 3, 4, 5, 6, 7, 8, 9, 10 or 11 chromogenic or fluorescent substrates.

A particular advantage of the composition according to the present invention is its great stability. In preferred embodiments the composition is stable for a period of up to 12 months, such as for a period of up to 11 months, a period of up to 11 months, up to 9 months, up to 8 months, up to 7 months, up to 6 months, up to 5 months, up to 4 months, up to 3 months, up to 2 months or such as for a period of up to 1 month when stored at a temperature of 4° C. or less.

A further aspect of the invention provides a platform for diagnosing, detecting and/or characterising a microbial infection or contamination comprising a composition as defined above.

In particular, the platform according to the invention may comprise a multiple of compositions as defined above, such as 2, 3, 4, 5, 6, 7, 8, 9, 10, 11, 12, 13, 14, 15, 20, 50, or 90 compositions, wherein at least 2 of the compositions comprises different antimicrobials, such as wherein at least 3, at least 4, at least 5, at least 6, at least 7, at least 8, at least 9, at least 10, at least 11, at least 12, at least 13, 14, 15, 20, 50 of the compositions comprises different antimicrobials or wherein each composition comprises a different antimicrobial.

In further embodiments the platform according to the invention comprises
i) a test composition that comprises a semi-solid microbial growth medium as defined above, and two or more chromogenic or fluorogenic substances (or substrates), such as a chromogenic or fluorogenic substance (or substrate) as defined above, and one or more antibiotics, such as one or more antibiotics as defined above;
ii) a control composition that comprises a semi-solid microbial growth medium as defined above, and two or more chromogenic or fluorogenic substances (or substrates), as defined above, but does not comprise an antimicrobial, such as an antimicrobial as defined above.

The control composition which does not comprise any antimicrobial, or which at least does not comprise any of the antimicrobials defined above (i.e. an antibiotic which is different from the antibiotic(s) present in the test composition), is useful for determining the number of micro-organisms as well as the species and/or groups of micro-organisms in a given sample. The test composition that comprises one or more antibiotics is useful for determining the susceptibility of these species and/or groups of micro-organisms to any antibiotic present in the test composition.

For the sake of convenience the platform according to the invention comprises a solid support, rendering the compositions according to the invention easy to handle.

In particular, the platform according to the invention may be based on a solid support, wherein said solid support comprises:
(i) an indentation (10) being capable of acting as a receptacle for a sample with a possible microbial infection or contamination, said indentation being divided into two or more separate compartments (11-16), each compartment containing a test composition as defined above or a control composition as defined above, that is a medium which does not comprise any of the antimicrobials mentioned above or which does not comprise any antimicrobials at all; and one or more integrated dividing members (17) for dividing said indentation into said separate compartments; or
(ii) multiple indentations (18), each indentation being capable of acting as a receptacle for a sample with a possible microbial infection or contamination, each containing a test composition as defined above or a control composition as defined above.

Figure 1B:
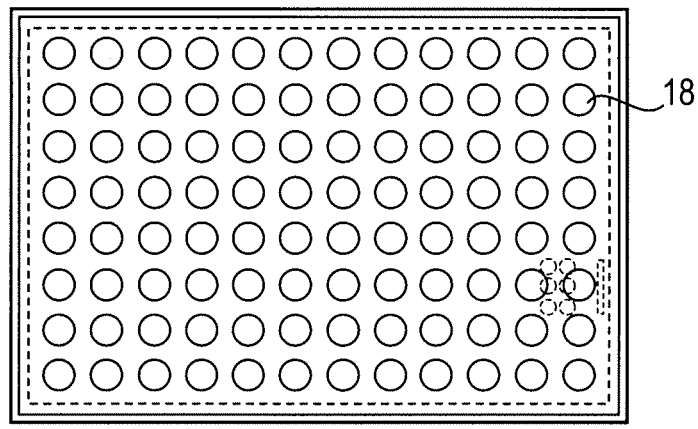
Figure 1B:

The numbers refer to the illustrations in FIG. 1, which are representative examples of platforms according to the present invention.

According to a preferred embodiment of the invention, the platform comprises test compositions containing antimicrobials selected from the group consisting of: Ampicillin/amoxicillin, Sulfonamide, Trimethoprim, Nitrofurantoin, Mecillinam, Ciprofloxacin (or other fluoroquinolone). According to this embodiment the platform may comprise one test composition comprising Ampicillin/amoxicillin, one comprising Sulfonamide, one comprising Trimethoprim, one comprising Nitrofurantoin, one comprising Mecillinam, and/or one comprising Ciprofloxacin (or other fluoroquinolone). Such a platform may be preferred for the purpose of diagnosing UTIs in Scandinavia.

Likewise the platform may comprise one test composition comprising rimethoprim, one comprising sulfamethizole, one comprising ampicillin, one comprising nitrofurantoin and one comprising mecillinam (amdinocillin).

For the purpose of diagnosing UTIs in the non-Scandinavian European countries a platform may be preferred comprising test compositions containing Amoxicillin, cluvulanic acid/ampicillin, sulbactam, Ciprofloxacin (or other fluoroquinolone), Sulphamethoxazole, trimethoprim, Cefalexin/cefuroxime/cefadroxil (or other oral cephalosporin), Nitrofurantoin and Fosfomycin (fosfomycin-trometerole).

Finally, for the purpose of diagnosing UTIs in North America/the United States a platform may be preferred comprising test compositions containing Amoxicillin, cluvulanic acid/ampicillin, sulbactam, Ciprofloxacin (or other fluoroquinolone), Sulphamethoxazole, trimethoprim, Cefalexin/cefuroxime/cefadroxil/cefaclor (or other oral cephalosporin), Nitrofurantoin and Fosfomycin (fosfomycin-trometerole)

In order to serve its purpose, the indentation or the said multiple indentations of the platform must have a volume sufficiently large to accommodate a suitable volume of sample. In particular embodiments indentation or the said multiple indentations has/have a depth of from 1-40 mm, such as from 1-35 mm, from 1-30 mm, from 1-25 mm, from 5-40 mm, from 5-35 mm, from 5-30 mm, from 5-25 mm, from 10-40 mm, from 10-35 mm, from 10-30 mm, from 10-25 mm, from 15-40 mm, from 15-35 mm, from 15-30 mm or such as from 25-25 mm.

For urinary tract infections as for many other infections particular policies apply concerning the use of diagnostics in general practice. General Practitioner treat the majority of patients experiencing UTI's and the antibiotic consumption for treatment of UTI amounts to about 25% of the total antibiotic use outside hospitals—and since 90% of the total amount of antibiotics used in a western society is used in the community, the antibiotic use for UTI is substantial. For the patient there is ample evidence that it is of benefit to receive the right diagnosis including bacterial susceptibility as early as possible. There are therefore many good reasons for the GP to perform the diagnosis of UTI at the clinic: It shortens the time to treatment by decreasing the transport time to a distant, central laboratory, and avoiding the transport improves the quality of the culture. Since the GP has little experience in microbiology, the method of culture should be easy to inoculate and read, and the susceptibility test should be independent of the inoculum and also easy to read, i.e. the GP or his assistant has little time to measure an inhibition zone and translate it into a susceptibility group. At the same time, the culture system should be easy to transport to the laboratory, if more sophisticated bacterial diagnostic workup is needed. Other important factors: The test should be able to measure and read counts down to $10^3$ CFU/ml, and it should be able to discern between pathogens and contaminants. All these factors are incorporated into platform according to the invention.

In order to meet these requirements the platform according to of the invention preferably has compartments with test compositions each of which has an area of from 4-9 $cm^2$, such as from 5-8 $cm^2$, from 6.5-7.5 $cm^2$. Likewise it is preferred that the compartment or compartments with control composition has an area of from 15-25 $cm^2$, such as from 17-23 $cm^2$, or from 19.5-21.5 $cm^2$.

The currently most preferred version of the platform has indentations or compartments with test compositions having an area of 6.93 $cm^2$ and a volume of 6.24 $cm^3$, and a compartment or an indentation with a control composition having an area of 20.78 $cm^2$ and a volume of 18.7 $cm^3$. This particular design is adapted to the use in detection, diagnosing and/ characterising urinary tract infections based on the experience that these areas and volumes are sufficient if the platform is to be used for detection of microbial infections, including urinary tract infections, in which the micro-organisms/bacteria are present in amounts of $10^3$ cfu/ml of sample/urine.

The said test and control compositions may be present in the respective indentations or compartments in an amount corresponding to from 5-75% of the volume of the indentation or compartment, such as from 10-75%, from 10-65%, from 10-55% from 10-45%, from 10-35%, from 20-75%, from 20-65%, from 20-55% from 20-45%, from 20-35% such as from 25-75%, from 25-65%, from 25-55% from 25-45%, from 25-35%, or such as in an amount corresponding to from 25-35% of the volume of the indentation or compartment.

In the platform according to the invention said indentation may, according to certain embodiments be divided into 3 or more compartments, such as 4 or more, 5 or more, 6 or more, 7 or more 8 or more, 9 or more, 10 or more, 15 or more, 20, or more, 40 or more, 60 or more or 90 or more compartments.

Further the platform according to the invention may have 3 or more indentations, such as 4 or more, 5 or more, 6 or more, 7 or more 8 or more, 9 or more; 10 or more, 15 or more, 20, or more, 40 or more, 60 or more or 90 or more indentations.

According to certain promising embodiments, the platform according to the invention comprises dividing members for dividing said indentation into separate compartments wherein said dividing members have been treated to prevent diffusion of an antimicrobial between the compartments. It is contemplated that surface tension present in the compositions according to the invention when they are poured into the indentations or wells of the platform is causing diffusion of antimicrobials between the compartments if great care is not taken. In order to avoid this said one or more dividing members may be polished so as to have a smooth surface. Other means for reducing the surface tension and diffusion of antimicrobials involve the addition of a detergent such as Tween to the compositions according to the invention.

Whereas many useful designs may be contemplated the said solid support is preferably in the form of a closed or open container, such as a tray, a test tube, a bottle, a multi-well plate, a microtiter plate, a stick (dipstick) or a slide.

The solid support may in particular be manufactured from a plastic/polymer substrate, such as a polyvinyl chloride substrate, a polyethylene substrate, a polypropylene substrate, a polycarbonate substrate, an acrylonitrile butadiene styrene substrate, a polymethyl metacrylate substrate or a polystyrene substrate, from a glass substrate or from a metal substrate.

According to presently preferred embodiments the platform according to the invention comprises a solid support, which is in the form of a Petri dish, such as a Petri dish having a diameter of from 50 to 150 mm, from 60-130 mm, from 70-110 mm or from 80-100 mm. According to one particular embodiment, the support is in the form of a 90 mm Petri dish.

The platform of the invention may be adapted to use in particular in the detection and/or diagnosis of infections selected from the group consisting of urinary tract infections, skin and soft tissue infections, infections with *S. aureus* (including methicillin resistant *S. aureus*), infections with meningococci, infections with gonococci and infections with streptococci.

Other tests may be incorporated into the platform, for instance glued to the internal surface of a lid covering said support, to the internal side of the support or onto a central part of the support, for instance a part where said dividing members coalesce. For use in such tests the platform may comprise an enzyme, such as a lecocyte esterase. When incorporated into the platform the lecocyte esterase enables the concomitant diagnosis of leucocyturia (could also be done for nitrite test). In accordance herewith the enzyme may be contained within a separate or an integrated member of said support. For example as previously described bacteria degrading L-tryptophan to indole can further be detected by addition of a paper disc to the lid of the petri dish. The disc prepared with Ehrlich-Bohme's reagent (Paradimethylaminobenzaldehyd dissolved in ethylalkohol/HCl) will give a red colour with indol vapour formed during incubation.

Another aspect of the invention provides kit comprising a composition as described above.

A related aspect provides a kit comprising a platform as described above.

Such kits may in a particular be for diagnosing, detecting and/or characterising a microbial infection or contamination.

Figure 3:
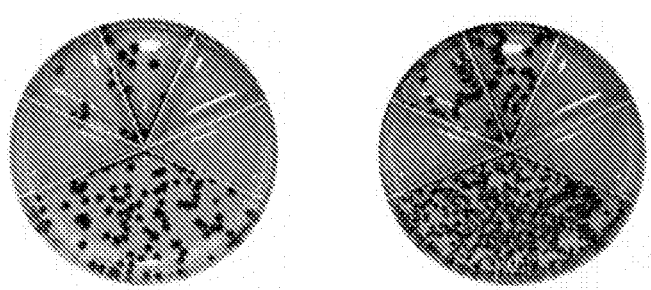
FIG. 3 shows a standard for determining the quantity or titre of *E. coli* in a sample analysed using the platform according a preferred embodiment of the invention (illustrated in FIG. 2). The photos show growth of *E. coli* at different quantities of bacteria/ml urine. The illustrated *E. coli* is resistant to sulfamethizole and ampicillin since there is growth in these two antibiotic compartments but it is susceptible to trimethoprim, nitrofurantoin and mecillinam.
Figure 3:
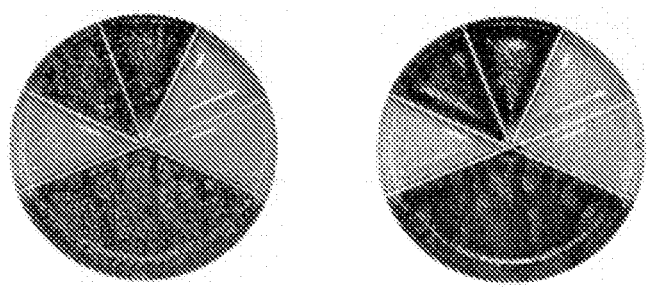
Figure 3:
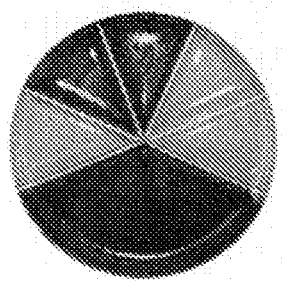

According to either aspect the kit may further comprise a standard illustrating the amount of growth on a platform as defined above, which results from contacting said platform with a suspension having a predetermined titre of a microbial reference strain. A representative standard is illustrated in FIG. 3 of the present application.

Figure 4:
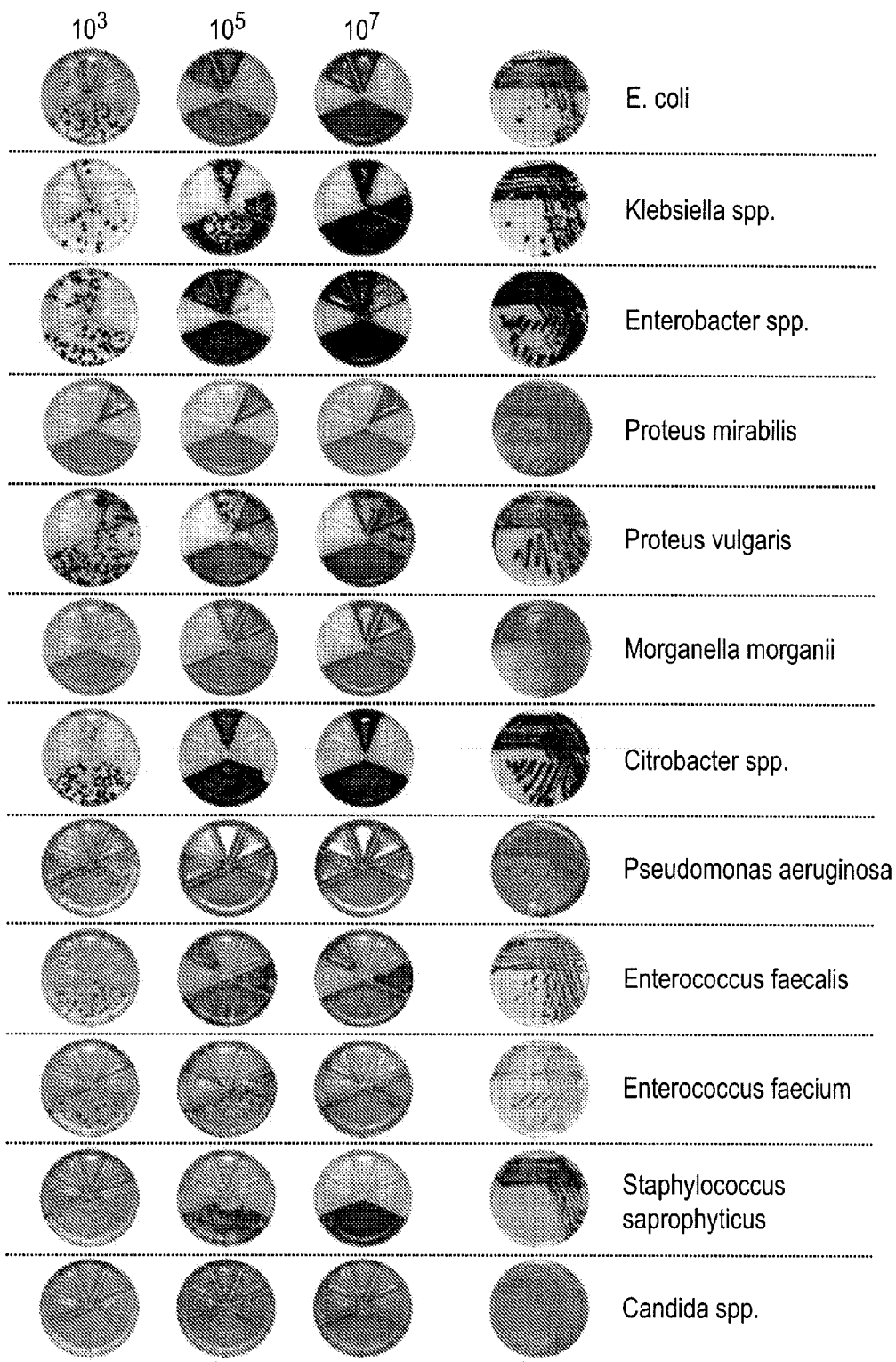
FIG. 4 shows a standard for determining the different colony types of urinary pathogens in a sample analysed using the platform according a preferred embodiment of the invention. Growth conditions and colours for ordinary urinary tract pathogenic bacteria and their susceptibility/resistance to the five antibiotics in the Flexicult plate are shown in FIG. 4 and described below in Table A.

The kit may also comprise a standard illustrating the development of biochemical pigment and/or fluorescence on a platform as defined above, which results from growth on the platform of one or more microbial reference strains. A representative standard is illustrated in FIG. 4 of the present application.

For the sake of convenience the standard is preferably a photographic or printed reproduction of a platform as defined above.

According to a particular embodiment the said standard illustrating the amount of growth on the platform has been generated by contacting a platform according to the invention with a reference strain of *E. coli* bacteria, such as *E. coli* (ATCC 29522) bacteria, and/or a reference strain of *Staphylococcus aureus*, such as *Staphylococcus aureus*, ATCC 25913.

According to a further particular embodiment the said standard illustrating the development of biochemical pigment and/or fluorescence on a platform has been generated by contacting a platform according to the invention with one or more reference strains selected from the group consisting of: *E. coli*, such as *E. coli* strain ATCC 25922, *K. pneumoniae*, such as *K. pneumoniae* strain ATCC 10031, *E. cloacae* such as *E. cloacae* strain ATCC 13047, *P. mirabilis* such as *P. mirabilis* strain ATCC 12453, *P. vulgaris* such as *P. vulgaris* strain ATCC 13315, *M. morganii* such as ATCC 25830, *C. freundii* such as *C. freundii* strain 8090, *P. aeruginosa* such as *P. aeruginosa* strain ATCC 27853, *E. faecalis* such as *E. faecalis* strain ATCC 29212, *E. faecium* such as *E. faecium* strain ATCC 35667, *S. saprophyticus* such as *S. saprophyticus* strain 49907, *C. albicans*, such as *C. albicans* strain ATCC 200955.

A standard which is useful in the context of the present invention is shown in FIG. 4.

The standards illustrating the amount of growth may be generated by a process comprising:
i) providing a suspension at a density of 0.5 McFarland/1+ E08 CFU/mL of said reference strain or reference strains in 0.9% brine;
ii) providing a series of 10-fold dilutions of said suspension in i), down to a density of +E03 CFU/mL;
iii) contacting each of said dilutions in ii) with a platform according to the invention for 2-3 seconds and subsequently decanting the solutions;
iv) incubating each platform over night at 35° C. at ambient atmosphere.

According to further embodiments, the kit comprises one or more separately packaged antimicrobials. Such one or more antibiotics may be included for on-site addition by the user to one or more compartments of the platform.

According to a currently preferred embodiment, the kit according to the invention is a kit for point-of-care diagnosis and susceptibility testing of urinary tract pathogens. The kit was developed for urine culture in the primary health care setting. It is designed preferably as a nine cm Petri dish divided into six compartments: One larger compartment for quantitative analysis and five smaller compartments for susceptibility testing. The agar in each small compartment contains one of five antimicrobials (for Denmark and Scandinavia preferably: trimethoprim, sulfamethizole, ampicillin, nitrofurantoin and mecillinam (amdinocillin)) at a concentration adjusted to the breakpoint, such that growth in these compartments indicates resistance, and no growth indicates susceptibility. The Petri dish preferably has higher sides, approximately 2.48 cm, than the usual dish, i.e. ca. 1.48 cm. This allows a larger amount, maximum 100 ml, of urine to be poured onto the dish for inoculation.

The agar in the plate is preferably composed of:
Chromogenic substances,
Isosensitest agar,
Antibiotics mixed in agar in five compartments:
Sulfamethizole
Trimethoprim
Ampicillin
Nitrofurantoin
Mecillinam An illustration of this embodiment is found in FIG. 2.

Inoculation occurs by pouring urine (5-10 ml is sufficient) over the plate and rotating the plate with one hand such that the fluid covers all six field. Hereafter the urine is poured off, presence of urine for 2-3 seconds is sufficient for inoculation. The plate is now incubated, preferably at 35-37° C. for 18-24 h (room temperature can be sufficient for most urinary pathogens, but growth will be slower). Reading of the plate falls in three phases: 1) evaluation of quantity of growth: If any growth is present it is compared with a picture scheme showing the different quantities of CFU's for *E. coli* at $10^3$, $10^4$, $10^5$, $10^6$, and $10^7$ CFU/ml. 2) The type of growth may now be evaluated, by comparing again with pictures/colour schemes showing the different types of urinary pathogens. Also the number of different colony types is noted, and the quantities of different colony types according to the above scheme. The bacterial families/species can be discerned by the colour and the colony type as illustrated in Table 5:

TABLE 5

Colour codes for colonies and agar of the different urinary pathogens on the Flexicult plate

| Species/group | Colour | Agar Colony (diameter in mm) |
|---|---|---|
| *E. coli* | | Salmon-red/pink |
| *Citrobacter* sp | | Greenish-blue |
| *Klebsiella/Enterobacter/Citrobacter* spp | | Dark-blue |
| *Proteus mirabilis/Morganella morganii* | Brown | Light brown |
| *Proteus vulgaris* | Brown | Dark green |
| *Enterococcus faecalis* | Green-blue | Greenish/blue (1-2 mm) |
| *Enterococcus faecium* | Green-blue | Greenish/blue (½-1 mm) |
| *Staphylococcus saprophyticus* | | Red/salmon-red |
| *Staphylococcus*, other | | White/yellow |
| *Pseudomonas aeruginosa* | Colour-less | (white/yellow - greenish after 24-36 h incubation) |
| *Candida* spp. | | White (hyphae after 48 h) |

Reading the susceptibility of the bacterial growth: Each bacterium (if more than one) is read individually: The growth in each of the antibiotic fields is compared with the growth on the control agar. If there is any growth on an antibiotic agar, and the amount of growth is similar to the control agar, then the bacterium is considered to be resistant to the antibiotic in the agar. If there is no growth (or substantially less than the control agar), then the bacterium is considered to be susceptible to the antibiotic. If there is more than no growth and less than substantially less growth, it is necessary to consider which antibiotic and which bacteria: For sulfamethizole and trimethoprim, which are bacteriostatic drugs, scanty minute colonies may cover the entire agar, but the growth is substantially reduced as compared to the control agar: this is recorded as susceptible to the antibiotic in question. When nitrofurantoin and mecillinam are used as antibiotics, a few single colonies may be seen of the same type as the bacterium on the control agar: These are not considered to be resistant mutants but "persisters," i.e. if retested they will appear susceptible. This is commonly seen also by disc diffusion especially for mecillinam.

4) The susceptibility/resistance of the different bacteria can also be used to diagnose the different pathogenic species, since some bacteria are "born" resistant to some antibiotics;

i.e. they are inherently resistant to one or more antibiotics in contrast to resistance bacteria acquire because they are exposed to antibiotics. These resistance-"pattern" can be seen in Table 6.

TABLE 6

Normal susceptibility/resistance of common urinary pathogens. Most of the bacteria can become resistant to the antibiotics in question by mutation or transfer of genes harbouring resistance-mechanisms

| | Susceptible = S, or Resistant = R | | | | |
|---|---|---|---|---|---|
| Bakterie | Trimetoprim | Sulfonamide | Ampicillin | Nitrofurantoin | Mecillinam |
| E. coli | S | S | S | S | S |
| Citrobacter | S | S | R | S | S |
| Klebsiella | S | S | R | S/R | S |
| Enterobacter | S | S | R | S/R | S |
| P. mirabilis | S | S | S | S/R | S/R |
| P. vulgaris | S | S | R | R | R |
| Morganella | S | S | R | R | R |
| S. saprophyticus | S | S | S | S | S/R |
| E. faecalis | S | R | S | S | R |
| E. faecium | S | R | S | S | R |
| S. agalactiae | S | S | S | S | R |
| Pseud. Aeruginosa | R | R | R | R | R |
| Candida sp. | R | R | R | R | R |

Yet another aspect of the invention provides the use of a composition according to the invention and as defined hereinbefore in the detection and/or diagnosis of infections selected from the group consisting of urinary tract infections, skin and soft tissue infections, infections with *S. aureus* (including methicillin resistant *S. aureus*), infections with meningococci, infections with gonococci, infections with streptococci including infections with pneumococci. In particular the invention provides the use of a said composition in the detection and or/identification of an uropathogenic microorganism.

Still another aspect provides a composition according to the invention and as defined hereinbefore, for use in detection and/or diagnosis of infections selected from the group consisting of urinary tract infections, skin and soft tissue infections, infections with *S. aureus* (including methicillin resistant *S. aureus*), infections with meningococci, infections with gonococci, infections with streptococci including infections with pneumococci.

The invention further provides a method of diagnosing, detecting and/or characterising a microbial infection or contamination comprising the steps of:
 i) providing a sample with a possible microbial infection or contamination; and
 ii) contacting said sample with a platform as defined above.

According to the invention is also provided a method of diagnosing, detecting and/or characterising a microbial infection or contamination comprising the steps of:
 i) providing a sample with a possible a microbial infection or contamination; and
 ii) contacting said sample with a test composition (such as two or more, 3 or more, 4 or more, 5 or more, 6 or more, or 7 or more test compositions) as defined herein before and with a control composition as also defined hereinbefore.

As it will be understood, the test composition, comprises a semi-solid microbial growth medium, two or more chromogenic or fluorogenic substances or substrates, and an antimicrobial. The control composition as explained above, comprises said semi-solid growth medium and said two or more chromogenic or fluorogenic substances (or substrates) but does not comprise any antimicrobial or comprises an antimicrobial different from the antimicrobial(s) present in the test composition.

The sample which is analysed in the method and by use of the composition, platform or kit according to the invention may be selected from the group consisting of: a sample of body fluid, a faecal sample, a mucous sample, a skin sample, a soft tissue sample, a sample of a food or food ingredient, a sample of an animal feed and a microbial (e.g. bacterial) pure culture.

In preferred embodiments in particular embodiments relating to diagnosing, detecting and/or characterising urinary tract infections, the sample is a urine sample.

The method so provided may further comprise a step of incubating said platform for a period of 10 hours or more, such as of 11 hours or more, 12 hours or more, 13 hours or more, 14 hours or more, 15 hours or more, 16 hours or more, 17 hours or more, or 18 hours or more preferably at a temperature of 15-39° C., and preferably at ambient atmosphere.

The method may further be characterised by comprising a step of visually inspecting the platform for microbial growth. This step of visually inspecting the compositions for microbial growth may in particular comprise:
 i) evaluating a quantity of any microbial growth on said control composition, optionally by reference to a standard showing different quantities of colony forming units; and
 ii) evaluating a type of any microbial growth on said control composition comprising said semi-solid growth medium and said two or more chromogenic or fluorogenic substances (or substrates) but not comprising any antimicrobial/antimicrobial different from the antimicrobial(s) present in the test composition, optionally by reference to a standard (such as a picture and/or colour scheme) illustrating growth of different groups or strains of microorganisms; and
 iii) determining antimicrobial susceptibility of said microbial growth by comparing the amount of growth on said test composition (such as two or more, 3 or more, 4, 5, 6, 7, 8, 9, 10, 11, 12, 13, 14, 15, 20, 30, 50 or 90 or more test compositions) with the amount of growth on said control composition.

Suitable standards showing different quantities of colony forming units and standards illustrating growth of different groups or strains of micro-organisms are described above.

The step of visually inspecting the compositions for microbial growth may further comprise determining the number of different colony types and optionally the quantity of colonies of each type on said test composition (such as on two or more, 3 or more, 4 or more, 5 or more, 6 or more or 7 or more compositions) as defined hereinbefore or on said control composition.

The method may further comprise determining whether a micro-organism in said sample is susceptible to an antimicrobial in said test composition, susceptibility being indicated by:
i) microbial growth being absent on said test composition or on one or more of said test compositions, while being present on said control composition; or
ii) microbial growth being present on said test composition or on one or more of said test compositions as well as on said control composition, the number of colonies/area on said test or on one or more of said test composition being at least 100 fold less than the number/area on said control composition.

In a further aspect the invention provides a method of manufacturing the composition according to the invention, comprising the step of combining a semi-solid microbial growth medium, two or more chromogenic or fluorogenic substances (or substrates), and an antimicrobial.

Likewise the invention disclosed a method of manufacturing a platform according to the invention, comprising the step of combining a semi-solid microbial growth medium, two or more chromogenic or fluorogenic substances (or substrates), and an antimicrobial.

Finally the invention provide a method of manufacturing the diagnostic kit according to the invention, comprising the step of combining a semi-solid microbial growth medium, two or more chromogenic or fluorogenic substances (or substrates), and an antimicrobial.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Preparation of a Platform Based on a 6-Compartment Petri Dish

Flexicult

Iso-sensitest agar was produced and combined with 1.5 g/l of a mixture of chromogenic substrate comprising 5-Bromo-4-chloro-3-indolyl-β-D-galactopyranoside, 6-Chloro-3-indolyl-β-D-galactopyranoside, 5-Bromo-4-chloro-3-indolyl-β-D-glucopyranoside, 5-Bromo-4-chloro-3-indolyl-β-D-glucuronide, 5-Bromo-6-chloro-3-indolyl-phosphate.

Alternatively Discovery agar (Oxoid, CM 1087) was used.

Antibiotic solutions were produced: trimethoprime, sulphamethizole, ampillicine, nitrofurantoine, and mecilliname.

Preparation of hot plates and temperature regulation via PT-100 sensor:
1. The bottles with Iso-sensitest/Discovery agar were melted at 105° C. for 60 min. After melting, the bottles were placed in a water bath at 56° C. for approx. 60 min.
2. The equipment for the filling of Flexicult was prepared: Variomag (Multitherm Stirring Block Thermostat and Telemodul 40 CT were interconnected and then connected to a socket. Telemodul 40 CT is the unit that controls both the temperature and the stirring speed of the heat block. The temperature was adjusted by means of a PT-100 sensor, which was installed at the back of the Telemodul 40 CT.
3. The bottles with Iso-sensitest/Discovery agar were taken from the water bath and placed on the Multitherm Stirring Block; each bottle was provided with a sterile magnet.
4. The cable for the PT-100 sensor was installed at the back of the Telemodul 40 CT, the contact point was singed and is then thoroughly wiped with a sterile cloth wetted with surgical spirits. The contact point was then placed in the flask with mecilliname. Telemodul 40 CT now adjusted the temperature in the agar to the required set point~approx. 50.0° C.±2.0° C. The speed of the magnetic stirrer was adjusted in relation to the contents of the flask (start): 235/min.

Preparation of Dispensers:
The dispensers were prepared (Fill-Master 251 and Fill-Master 311). To the Fill-Master 251 was attached one 4 mm sterile silicone tube and to the Fill-Master 311 were attached five 2 mm sterile silicone tubes. The respective dispensers were set at the right tube size (2 mm and 4 mm, respectively).

The filling volume was set so that the filled volume+the weight of the dish are in the range of 31-33 g. This was checked regularly.

Addition of the Antibiotic Solutions:
Note: The 5 antibiotic solutions should not be added to the agar until the temperature is below 54.0° C. The temperature of the agar was checked in the display of the Telemodul CT 40.

Trimethoprime (16 μg/mL):
The trimethoprime stock solution was added with a graduated pipette to the Iso-sensitest/Discovery agar.
The solution was thoroughly mixed on the Multitherm hot plate. The suction hose was placed in the bottle and was connected to the correct filling needle.

Sulphamethizole (700 μg/mL):
The sulphamethizole stock solution was added with a graduated pipette to the Iso-sensitest/Discovery agar.
The solution was thoroughly mixed on the Multitherm hot plate. The suction hose was placed in the bottle and is connected to the correct filling needle.

Ampicilline (32 μg/mL).
The ampicilline stock solution was then added with a graduated pipette to the Iso-sensitest/Discovery agar.
The solution was thoroughly mixed on the Multitherm hot plate. The suction hose was placed in the bottle and was connected to the correct filling needle.

Nitrofurantoine (32 μg/mL):
The nitrofurantoine stock solution was assess with a graduated pipette to the Iso-sensitest/Discovery agar.
The solution was thoroughly mixed on the Multitherm hot plate. The suction hose was placed in the bottle and is connected to the correct filling needle.

Mecilliname (16 μg/mL):
The mecilliname stock solution was then added with a graduated pipette to the Iso-sensitest/Discovery agar.
The solution was thoroughly mixed on the Multitherm hot plate. The suction hose was placed in the bottle and was connected to the correct filling needle.

Iso-Sensitest/Discovery Agar, without Antibiotics:
The suction hose is placed in the bottle and was connected to the correct filling needle.

Figure 2:
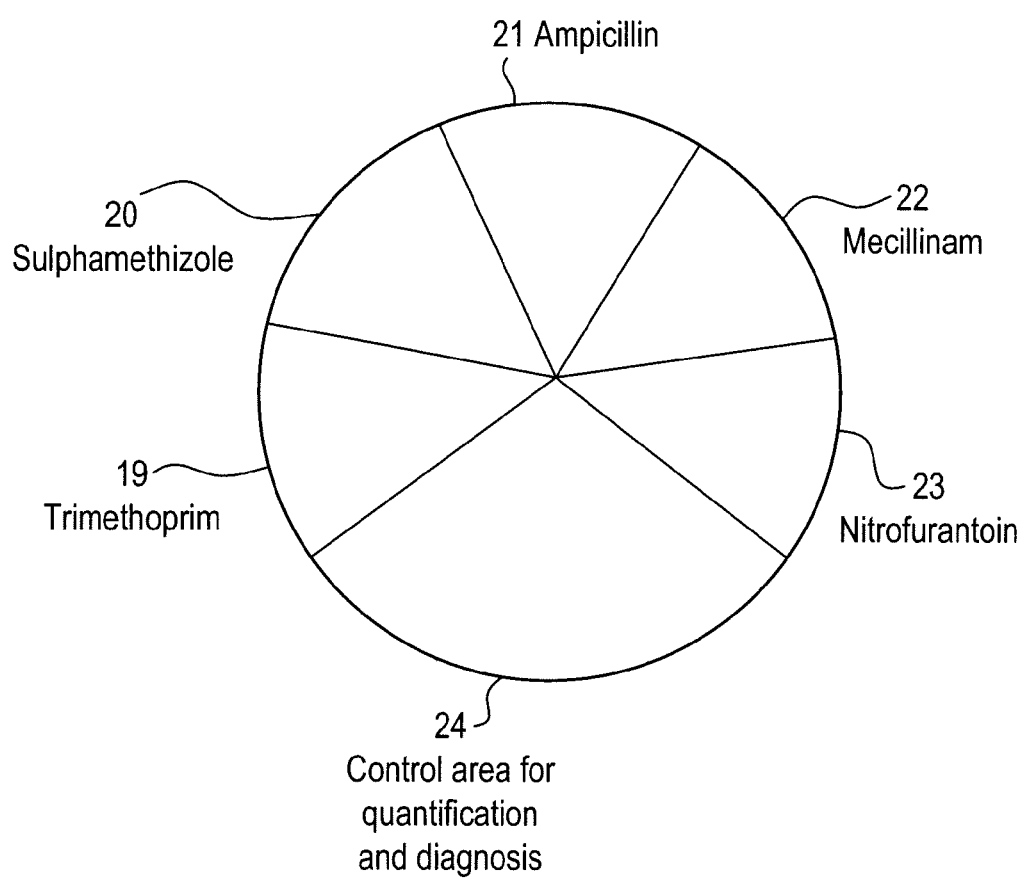
FIG. 2 illustrates one of the presently preferred embodiments of the invention according to which the platform comprises a composition according to the inventions comprising Trimethoprim (19), a composition according to the inventions comprising Sulphamethizole (20) a composition according to the inventions comprising Ampicillin (21), a composition according to the inventions comprising Mecilinam (22) and a composition according to the inventions comprising Nitrofurantoin (23). The platform further comprises a composition according to the invention in which there is no antimicrobial (24). Finally, the figure illustrates yet a preferred embodiment according to which the indentation or compartment containing said composition not comprising an antimicrobial has a size which is twice the size of any of the other indentations or compartments.

Filling of the Petri Dish in 6 Parts:

The 6 filling needles were placed in the dispenser head ensuring that the dosage corresponds to FIG. 2.

Example 2

Stability Test

The stability of the chromogenic agar in Flexicult has been determined by testing Flexicult agars kept up to 4 months in refrigerator (<4° C.) and tested for growth conditions (quantity, colony size, colour of colonies and agar) at 1, 2, 3 and 4 months after production for clinical strains of all the bacteria mentioned in Table 2, and the same results were seen for up to 4 months after production (as present at day 1 after production) regarding:
- Agar stability (water content/dryness, form)
- Colourisation of bacterial colonies
- Susceptibility/resistance towards the antibiotics (sulfamethizole, trimethoprim, ampicillin, nitrofurantoin and mecillinam.

Example 3

Clinical Validation

The Flexicult agar kit has been tested in two GP clinics. Both clinics have 9-10 GP's working in the clinic and perform routine urine culture (either by dipslide or agar plate with subsequent antibiotic disc diffusion susceptibility in certain cases), performed by clinical biochemistry technician staff.

For the study, the Flexicult plate was inoculated with urine from patients with suspected UTI as based on history and symptoms in parallel with the routine culture systems for each clinic. The plates were incubated at 35-37° C. in ambient atmosphere for 18-24 h (tests performed Friday, which could not be read Saturday, were not included). Plates were read by the technicians and the results recorded (by the use of material provided together with the plates from the Statens Serum Institut: A picture scheme showing the quantities of bacteria on the Flexicult plate, see FIG. 3, and a picture scheme showing the different colony types of urinary pathogens, see FIG. 4). Hereafter the plates were transported to the National Center for Antimicrobials and Infections Control, Statens Serum Institut, where the plates were read again, and from plates with relevant growth of one or two potential urinary pathogens colonies were processed for diagnosis using API-20E, Vitec or biochemical tests according to laboratory routine. Further, for all relevant bacteria the MIC towards sulfamethizole, trimethoprim, ampicillin, nitrofurantoin and mecilinam were determined by agar dilution in Mueller-Hinton agar according to CSLI (former NCCLS).

Results: The diagnoses of the bacteria are recorded in Table 7, showing the tentative and the actual diagnosis, and the percentage correct diagnoses (to the group or species level).

TABLE 7

Results of clinical validation trial, tentative diagnosis at reading of the test as compared with the subsequent final diagnosis of the bacteria.

|  | Total | Wrong diagnosis No. isolates | Correct diagnosis No. isolates | Correct diagnosis % of total |
|---|---|---|---|---|
| E. coli | 205 | 16 | 189 | 92.2 |
| Klebsiella/ Enterobacter sp | 23 | 0 | 23 | 100.0 |
| Prot/Morg | 19 | 4 | 15 | 78.9 |
| Enterobacteriaceae, other | 4 | 4 |  | 0 |
| Ps. aeruginosa | 6 | 0 | 6 | 100.0 |
| E. faecalis | 67 | 1 | 66 | 98.5 |
| Gr. B strep | 12 | 9 | 3 | 25.0 |
| S. saprophyticus | 6 | 0 | 6* | 100.0 |
| A. viridans | 2 | 1 | 1 | 50.0 |
| other | 22 | 12 | 10 | 45.4 |
| Candida | 23 | 0 | 23 | 100.0 |
| Total | 389 | 47 | 342 | 88 |

Regarding the determination of susceptibility, i.e. comparing the measured MIC's with reading of the test, of the bacteria, Tables 7 and 8 show the results for the Gram-negative bacteria in Table 8 and the Gram-positive bacteria in Table 9. The results have been analysed according to whether the reading and reporting of the result could be classified as an error (i.e. the result being S for I, I for R, R for I or I for S), a major error (i.e. recorded as R but was actually S, which means that the patient could be treated with another drug) and very major error (i.e. reported as S but was R, which could carry the risk that the patient was treated with an antibiotic that did not have effect).

TABLE 8

Results of reading the susceptibility/resistance of Gram-negative bacteria growing on the Flexicult agar as compared to the subsequently determined MIC by agar-dilution. Numbers indicate number of strains with recorded result (% of total).

|  | Trimethoprim N = 248 | Sulfametizol N = 231 | Ampicilin N = 247 | Nitrofurantoin N = 183 | Mecillinam N = 246 |
|---|---|---|---|---|---|
| Error S/R > < I | 0 | 1 (0.4%) | 2 (0.8%) | 3 (1.6%) | 11 (4.5%) |
| Major error R > < S | 2 (0.8%) | 7 (3.0%) | 5 (2.0%) | 4 (2.2%) | 17 (6.9%) |
| Very major error S > < R | 2 (0.8%) | 1 (0.5%) | 1 (0.4%) | 8* (4.4%) | 1 (0.4%) |

TABLE 9

Results of reading the susceptibility/resistance of Gram-Positive bacteria growing on the Flexicult agar as compared to the subsequently determined MIC by agar-dilution. Numbers indicate number of strains with recorded result (% of total).

| | Trimethoprim | Sulfametizol | Ampicilin N = 26 | Nitrofurantoin N = 26 | Mecillinam |
|---|---|---|---|---|---|
| Error S/R > < I | — | — | 0 (0%) | 0 (0%) | — |
| Major error R > < S | — | — | 1 (3.8%) | 0 (0%) | — |
| Very major error S > < R | — | — | 0 (0%) | 0 (0%) | — |

Conclusion of Clinical Validation:

The results show a high degree of precision of the Flexicult regarding diagnosis to the group or species level of urinary pathogens. Also, the result of the susceptibility test incorporated in the Flexicult test is comparable to a disc-diffusion test by having <5% very major errors. Certainly, the test can be used to diagnose UTI in a patient by finding the quantity of the bacteria at all relevant counts, to diagnose the urinary pathogen (up to almost 90% of the pathogens were correctly diagnosed to the group or species level). A retest of a patient with former UTI would help showing whether the same or a new type of pathogen was present i.e. it would within certain limits be possible to discern between a relapse or a new infection. When including the susceptibility of the isolate in question, this could help in the diagnosis of a possible relapse/reinfection by viewing the "resisto-type" of the isolates found.

Example 4

Flexicult vs. Other Diagnostic Methods in Primary Care

Comparing the Flexicult with other available methods for diagnosis in general practice and susceptibility testing of urinary pathogens:

TABLE 10

Comparison of different diagnostic tests for UTI in primary care.

| Test | Level of CFU/ml | Speed of result for Possible diagnosis and susceptibility | Diagnosis of pathogen | Susceptibility test directly | Comment |
|---|---|---|---|---|---|
| Microscopy | $10^5$ | NA* | NA | NA | |
| Dipstick (nitrite/Leucocyte) | $10^5$ | NA | NA | NA | |
| Dipslide | $10^3$ | | Yes, Some dipslides use Chromogenic agar | NA | Poor PPV of susc. test |
| Agar Plate with Subs. Disc diffusion | Depend on loop | 3 days | NA | NA | |
| Flexicult | $10^3$ | 2 days | Yes | Yes | |

*NA, not applicable

REFERENCES (1) Laupland K B et al. *Infection,* 2007, 35: 150-3.
(2) Kass E H *Ann Intern Med.* 1962, 56:46-53.
(3) Stamm W E et. al. *N Engl J Med* 1982, 307(8):463-468.
(4) Frimodt-Møller N et al. *Ugeskr Loeger* 1989, 151: 3062-4
(5) Frimodt-Møller N et al *APMIS* 2000, 108: 525-30.
(6) Mabeck C E. *Postgraduate Medical Journal* 1972, 48:69-75.
(7) Ferry S et al *Scand J Prim Health Care* 1989, 7: 123-128
(8) Zhanel G G et al. *Int J Antimicrob Agents.* 2006, 27: 468-75.
(9) Kahlmeter G et al. *J Antimicrob Chemother.* 2003, 51: 69-76.

What is claimed is:

1. A platform comprising a solid support that comprises six or more separate compartments, each compartment comprising a test composition or a control composition, wherein
   i) said test composition comprises a semi solid microbial growth medium, an antibacterial antibiotic, and three or more chromogenic substrates selected from the group consisting of 5-Bromo-6-chloro-3-indolyl phosphate p-toluidine, 5-Bromo-4-chloro-3-indolyl-β-D-galactopyranoside, 5-Bromo-6-chloro-3-indolyl-β-D-galactopyranoside, 6-Chloro-3-indolyl-β-D-galactopyranoside, 5-Bromo-4-chloro-3-indolyl-β-D-glucopyranoside, and 5-Bromo-4-chloro-3-indolyl-β-D-glucuronide;
   ii) at least five of said compartments comprise test compositions, each test composition differing from the others by comprising a different antibacterial antibiotic;
   iii) at least one of said compartments comprises a control composition; said control composition comprises the same semi solid microbial growth medium and the same chromogenic substrates as said test composition, but does not comprise an antibacterial antibiotic as defined in i); and wherein said semi solid microbial growth medium comprises tryptophan.

2. The platform according to claim 1, wherein said platform comprising
  i) a test composition that comprises a semi-solid microbial growth medium comprising tryptophan, and three or more chromogenic substances selected from the group consisting of: 5-Bromo-6-chloro-3-indolyl phosphate p-toluidine, 5-Bromo-4-chloro-3-indolyl-β-D-galactopyranoside, 5-Bromo-6-chloro-3-indolyl-β-D-galactopyranoside, 6-Chloro-3-indolyl-β-D-galactopyranoside, 5-Bromo-4-chloro-3-indolyl-β-D-glucopyranoside, and 5-Bromo-4-chloro-3-indolyl-β-D-glucuronide and an antibacterial antibiotic antimicrobial selected from the group consisting of: Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Mezlocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, Voriconazole
  ii) a control composition that comprises a semi-solid microbial growth medium comprising tryptophan, and three or more chromogenic substances selected from the group consisting of: 5-Bromo-6-chloro-3-indolyl phosphate p-toluidine, 5-Bromo-4-chloro-3-indolyl-β-D-galactopyranoside, 5-Bromo-6-chloro-3-indolyl-β-D-galactopyranoside, 6-Chloro-3-indolyl-β-D-galactopyranoside, 5-Bromo-4-chloro-3-indolyl-β-D-glucopyranoside, and 5-Bromo-4-chloro-3-indolyl-β-D-glucuronide.

3. The platform according to claim 1, wherein said compartments have a depth of from 10-25 mm.

4. The platform according to claim 1, wherein said composition is present in each of said compartments in an amount corresponding to from 25-45% of the volume of the compartment.

5. The platform according to claim 1, said platform having 7 or more compartments.

6. The platform according to claim 1, wherein said compartments are separated by dividing members that have been treated to prevent diffusion of an antibacterial antibiotic between the compartments.

7. The platform according to claim 1, wherein said solid support is manufactured from a plastic/polymer substrate, from a glass substrate or from a metal substrate.

8. The platform according to claim 1, wherein said solid support is a Petri dish.

9. A method comprising detecting uropathogenic microorganisms using the platform of claim 1.

10. A method comprising detecting infections selected from the group consisting of urinary tract infections, skin and soft tissue infections, infections with *S. aureus* (including methicillin resistant *S. aureus*), infections with meningococci, infections with gonococci, infections with streptococci including infections with pneumococci using the platform of claim 1.

11. A method of diagnosing, detecting and/or characterising a microbial infection or contamination comprising the steps of:
  i) providing a sample with a possible microbial infection or contamination; and
  ii) contacting said sample with a platform as defined in claim 1.

12. The method according to claim 11, comprising determining whether a micro-organism in said sample is susceptible to an antibacterial antibiotic in said test composition, susceptibility being indicated by:
  ii) microbial growth being absent on said test composition or on one or more of said test compositions, while being present on said control composition, or
  iii) microbial growth being present on said test composition or on one or more of said test compositions as well as on said control compositions, the number of colonies/area on said test or on one composition being at least 100 fold less than the number/area on said first composition.

13. A method of manufacturing the platform according to claim 1, comprising the step of combining a semi-solid microbial growth medium, three or more chromogenic substrates, and an antibacterial antibiotic.

14. The platform according to claim 1, wherein each of said compartments comprising a test composition has an area of from 4-9 $cm^2$.

15. The platform according to claim 1, wherein said compartment comprising a control composition has an area of from 15-25 $cm^2$.

16. The platform according to claim 1, wherein said solid support is a Petri dish, having a diameter of from 80 to 100 mm.

17. The platform according to claim 1, said platform comprising one or more substrates for β-galactosidase and one or more substrates for β-glucosidase.

18. The platform according to claim 1, wherein said test composition and said control composition comprise one or more inducers.

19. The platform according to claim 18, wherein said one or more inducers are selected from the group consisting of 4-aminophenyl-β-D-galactopyranoside, isopropyl-β-D-thiogalactopyranoside, 1-O-Methyl-β-D-galactopyranoside, Methyl-β-D-thiogalactopyranoside, 1-o-Methyl-α-D-galactopyranoside, Isopropyl-β-D-thioglucopyranoside, 1-O-methyl-β-D-glucopyranoside, Isopropyl-β-D-thioglucouronic acid, 1-O-Methyl-β-D-glucouronic acid, sodium salt.

20. The platform according to claim 1, wherein said 3 or more chromogenic substrates comprise 5-Bromo-4-chloro-3- indolyl-β-D-galactopyranoside, 6-Chloro-3-indolyl-β-D-galactopyranoside, 5-Bromo-4-chloro-3-indolyl-β-D-glucopyranoside.

21. The platform according to claim 1, wherein said test composition and said control composition comprises Isopropyl-β-D-thiogalactopyranoside or 1-o-Methyl-beta-D-glucopyranoside.

22. The platform according to claim 1, wherein
   i) any colonies of *E. coli*, if present, will appear Salmon-red/pink;
   ii) any colonies of *Citrobacter* sp., if present, will appear greenish-blue;
   iii) any colonies of *Klebsiella, Enterobacter* or *Citrobacter* spp., if present, will appear dark blue;
   iv) any colonies of *Proteus mirabilis/Morganella morganii*, if present, will appear light brown;
   v) any colonies of *Proteus vulgaris*, if present, will appear dark green;
   vi) any colonies of *Enterococcus faecalis* or *Enterococcus faecium*, if present, will appear greenish or blue;
   vii) any colonies of *Staphylococcus saprophyticus*, if present, will appear red or salmon-red;
   viii) any colonies of *Staphylococcus* or *Pseudomonas aeruginosa*, if present, will appear white or yellow; and
   ix) any colonies of *Candida* spp. will appear white.

23. The platform according to claim 1, wherein said antibacterial antibiotic is selected from the group consisting of Amoxicillin, cluvulanic acid/ampicillin, sulbactam, a fluoroquinolone, Sulphamethoxazole, trimethoprim, an oral cephalosporin, Nitrofurantoin and Fosfomycin (fosfomycin-trometerole).

24. The platform according to claim 23, wherein said fluoroquinolone is Ciprofloxacin.

25. The platform according to claim 23, wherein said oral cephalosporin is selected from the group consisting of Cefalexin, cefuroxime, cefadroxil and cefaclor.

26. The platform according to claim 1, wherein said semi solid microbial growth medium is selected from the group consisting of:
   i) A medium composed of: 11 g/l Hydrolysed casein, 3 g/l Peptones, 2 g/l Glucose, 3 g/l Sodium Chloride, 1 g/l soluble starch, 2 g/l Disodium hydrogen Phosphate, 1 g/l Sodium Acetate, 0.2 g/l Magnesium glycerophosphate, 0.1 g/l Calcium gluconate, 0.001 g/l cobaltous sulphate, 0.001 g/l Cupric sulphate, 0.001 g/l Zinc sulphate, 0.001 g/l Ferrous Sulphate, 0.002 g/l Magnesium Chloride, 0.001 g/l Menadione, 0.001 g/l Cyanobalamin, 0.02 g/l L-Cysteine hydrochloride, 0.02 g/l Tryptophan, 0.003 g/l pyridoxine, 0.003 g/l pantothenate, 0.003 g/l nicotinamide, 0.0003 g/l Biotin, 0.00004 g/l Thiamine, 0.01 g/l Adenine, 0.01 g/l Guanine, 0.01 g/l Xanthine, 0.01 g/l Uracil, and 8 g/l agar, in distilled water;
   ii) A medium composed of: 2 g Na2HPO4.12 H2O, 625 g tryptone, 250 g starch, 833.6 g Potassium Chloride, 2.5 g detergent, 74.8 g meat broth (Oxoid CM975K), 800 g D(+)Glucose-monohydrate, 1.75 g Xanthin, 1.75 g Guanin, 17.5 g Magnesium Sulphate 7 H2O, 19.2 g CaCl$_2$.2 H2O, 2,720 g Agar, 5 N HCl to pH 7.4, solution of vitamins, and 12.5 l horse blood per 250 liter distilled water;
   iii) A medium comprising: 14.5 g/l Peptone, 2 g/l glucose, 5.5 g/l salt mix, 1 g/l Soluble starch, 1.5 g/l chromogenic mix, and 8 g/l Agar; and
   iv) A medium comprising: 2 g/l Beef extract powder/beef extract, 17.5 g/l Acid Digest of Casein, 1.5 g/l starch and 17 g/l Agar;
   wherein the amount of each component in said medium may be varied by ±20%.

27. The platform according to claim 1, wherein said test composition and said control composition comprises 6-Chloro-3-indolyl-β-D-galactopyranoside in combination with 5-Bromo-4-chloro-3-indolyl-β-D-glucopyranoside and 5-Bromo-6-chloro-3-indolyl-β-D-galactopyranoside.

28. The platform according to claim 1, wherein said test and said control composition comprises 6-Chloro-3-indolyl-β-D-galactopyranoside in combination with 5-Bromo-4-chloro-3-indolyl-β-D-glucopyranoside, 5-Bromo-4-chloro-3-indolyl-β-D-glucuronide, 5-Bromo-4-chloro-3-indolyl-β-D-galactopyranoside and 5-Bromo-6-chloro-3-indolyl phosphate p-toluidine.

29. The platform according to claim 1, wherein said test composition and said control composition comprise four chromogenic substrates.

30. The platform according to claim 1, wherein said semi solid microbial growth medium comprises 0.25-3.0 g/l tryptophan is present.

31. The platform according to claim 1, wherein one or more inducers are present in said test composition and in said control composition in amounts of 0.001 to 1.0 g/l.

32. The platform according to claim 1, wherein said solid support is a Petri dish divided into 5 test compartments and 1 control compartment.

33. The platform according to claim 1, wherein the platform is capable of identifying the presence and quantity of *E. Coli, Klebsiella* spp., *Enterobacter* spp., *Proteus mirabilis, Proteus vulgaris, Morganella morganii, Citrobacter* spp., *Pseudomonas aeruginosa, Enterococcus faecalis, Enterococcus faecium, Staphylococcus saprophyticus*, and *Candida* spp. in a urine sample.

34. The platform according to claim 1, wherein the antibacterial antibiotic is selected from the group consisting of aminoglycosides, ansamycins, beta-lactam antibiotics, glycopeptides, macrolides, lincosamides, polypeptides, quinolones, sulphonamides, tetracyclines, cyclic lipopeptides, glycylcyclines, oxazolidinones, diaminopyrimidines, nitrofurans, rifamycins, antibiotic peptides, amphenicols, nitroimidazoles, streptogramins and phosphomycins.

35. A kit comprising a platform according to claim 1.

36. The kit according to claim 35, said kit further comprising a standard illustrating the amount of growth on a platform as defined in claim 1, which results from contacting said platform with a suspension having a predetermined titre of a microbial reference strain.

37. The kit according to claim 36, wherein said standard is a photographic or printed reproduction of a platform as defined in claim 1.

38. The kit according to claim 36, wherein said standard has been generated by contacting a platform as defined in claim 1 with
   i) a reference strain of *E. coli* bacteria and/or a reference strain of *Staphylococcus aureus*.

39. The kit according to claim 38, wherein said reference strain of *E. coli* bacteria is *E. coli* ATCC 29522.

40. The kit according to claim 38, wherein said reference strain of *Staphylococcus aureus* is *Staphylococcus aureus* ATCC 25913.

41. The kit according to claim 35, said kit further comprising one or more separately packaged antibacterial antibiotics.

42. A method of manufacturing the diagnostic kit according to claim 35, comprising the step of combining a semi-solid microbial growth medium, three or more chromogenic substrates, and an antibacterial antibiotic.

43. A method of diagnosing, detecting and/or characterizing a microbial infection or contamination comprising the steps of:
i) providing a sample with a possible a microbial infection or contamination; and
ii) contacting said sample with a test composition as defined in claim 2 i), comprising a semi-solid microbial growth medium, three or more chromogenic substrates, and an antibacterial antibiotic, and with a control composition as defined in claim 2 ii) comprising said semi-solid growth medium and said three or more chromogenic substrates but not comprising any antibacterial antibiotic.

44. The method according to claim 43, wherein said sample is selected from the group consisting of: a sample of body fluid, a faecal sample, a mucous sample, a skin sample, a soft tissue sample, a sample of a food or food ingredient, a sample of an animal feed and a microbial (e.g. bacterial) pure culture.

45. The method according to claim 43, wherein said sample is a urine sample.

46. The method according to claim 43, said method comprising the additional steps of incubating said platform for a period of 18 hours or more at a temperature of 15-37° C., preferably at ambient atmosphere.

47. The method according to claim 43, said method comprising visually inspecting the platform for microbial growth.

48. The method according to claim 47, wherein said step of visually inspecting the compositions for microbial growth comprises:
i) evaluating a quantity of any microbial growth on said control composition, optionally by reference to a standard showing different quantities of colony forming units; and
selected from the group consisting of 5-Bromo-6-chloro-3-indolyl phosphate p-toluidine, 5-Bromo-4-chloro-3-indolyl-β-D-galactopyranoside, 5-Bromo-6-chloro-3-indolyl-β-D-galactopyranoside, 6-Chloro-3-indolyl-β-D-galactopyranoside, 5-Bromo-4-chloro-3-indolyl-β-D-glucopyranoside, and 5-Bromo-4-chloro-3-indolyl-β-D-glucuronide, but does not comprise an antibacterial antibiotic selected from the group consisting of: Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Mezlocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, Voriconazole ii) comprising said semi-solid growth medium and said three or more chromogenic substrates but not comprising any antibacterial antibiotic optionally by reference to a standard illustrating growth of different groups or strains of microorganisms; and
selected from the group consisting of 5-Bromo-6-chloro-3-indolyl phosphate p-toluidine, 5-Bromo-4-chloro-3-indolyl-β-D-galactopyranoside, 5-Bromo-6-chloro-3-indolyl-β-D-galactopyranoside, 6-Chloro-3-indolyl-β-D-galactopyranoside, 5-Bromo-4-chloro-3-indolyl-β-D-glucopyranoside, and 5-Bromo-4-chloro-3-indolyl-β-D-glucuronide, but does not comprise an antibacterial antibiotic selected from the group consisting of: Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Mezlocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, Voriconazole i) with the amount of growth on said control composition, optionally by reference to a standard.

49. The method according to claim 47, wherein said step of visually inspecting the compositions for microbial growth comprises determining the number of different colony types and optionally the quantity of colonies of each type on said composition comprising a semi-solid microbial growth medium, three or more chromogenic substrates, and an antibacterial antibiotic or on said control composition.

50. The method according to claim 48, wherein said standard is a standard as defined in claim 36.

51. A platform comprising a solid support that comprises at least 5 separate test compartments, each having an area of 4-9 cm$^2$, and at least one control compartment having an area of 15-25 cm$^2$, wherein
- i) each of said test compartments comprises a test composition comprising a semi solid microbial growth medium, an antibacterial antibiotic selected from the group consisting of aminoglycosides, ansamycins, beta-lactam antibiotics, glycopeptides, macrolides, lincosamides, polypeptides, quinolones, sulphonamides, tetracyclines, cyclic lipopeptides, glycylcyclines, oxazolidinones, diaminopyrimidines, nitrofurans, rifamycins, antibiotic peptides, amphenicols, nitroimidazoles, streptogramins and phosphomycins,
and
three or more chromogenic substrates selected from the group consisting of 5-Bromo-6-chloro-3-indolyl phosphate p-toluidine, 5-Bromo-4-chloro-3-indolyl-O-D-galactopyranoside, 5-Bromo-6-chloro-3-indolyl-β-D-galactopyranoside, 6-Chloro-3-indolyl-β-D-galactopyranoside, 5-Bromo-4-chloro-3-indolyl-β-D-glucopyranoside, 5-Bromo-4-chloro-3-indolyl-β-D-glucuronide;
- ii) each test composition differs from the others only by comprising a different antibacterial antibiotic;
- iii) said control compartment comprises a control composition which comprises the same semi-solid microbial growth medium and the same chromogenic substrates as said test composition, but does not comprise said antibacterial antibiotic as defined in i);

and wherein said semi solid microbial growth medium comprises tryptophan.

52. The platform according to claim 51, wherein each of said test compartments has an area of 5-8 cm$^2$ and said control compartment has an area of 17-23 cm$^2$.

53. The platform according to claim 51, wherein said test composition and said control composition comprises 6-Chloro-3-indolyl-β-D-galactopyranoside in combination with 5-Bromo-4-chloro-3-indolyl-β-D-glucopyranoside and 5-Bromo-6-chloro-3-indolyl-β-D-galactopyranoside.

54. The platform according to claim 51, wherein said test and said control composition comprises 6-Chloro-3-indolyl-β-D-galactopyranoside in combination with 5-Bromo-4-chloro-3-indolyl-β-D-glucopyranoside, 5-Bromo-4-chloro-3-indolyl-β-D-glucuronide, 5-Bromo-4-chloro-3-indolyl-β-D-galactopyranoside and 5-Bromo-6-chloro-3-indolyl phosphate p-toluidine.

55. The platform according to claim 51, wherein said test composition and said control composition comprise one or more inducers selected from the group consisting of 4-aminophenyl-β-D-galactopyranoside, isopropyl-β-D-thiogalactopyranoside, galactopyranoside, Methyl-β-D-thiogalactopyranoside, 1-O-Methyl-α-D-galactopyranoside, Isopropyl-β-D-thioglucopyranoside, 1-O-methyl-β-D-glucopyranoside, Isopropyl-β-D-thioglucouronic acid, 1-O-Methyl-β-D-glucouronic acid, sodium salt.

56. The platform according to claim 51, wherein said one or more inducers are selected from isopropyl-β-D-thiogalactopyranoside and 1-O-methyl-β-D-glucopyranoside.

57. The platform according to claim 51, wherein said solid support is a Petri dish having a diameter of 80-100 mm.

58. The platform according to claim 51, wherein said compartments have a depth of 10-25 mm.

59. The platform according to claim 51, wherein said test and control compartments are separated from each other by dividing members, which have been polished so as to prevent diffusion of antibacterial antibiotics between the compartments and/or where said test compositions comprise a detergent in amounts capable of reducing the surface tension and prevent diffusion of antibacterial antibiotics between the compartments.

* * * * *

UNITED STATES PATENT AND TRADEMARK OFFICE
CERTIFICATE OF CORRECTION

PATENT NO. : 8,753,875 B2
APPLICATION NO. : 12/198542
DATED : June 17, 2014
INVENTOR(S) : Frimodt-Møller Page 1 of 1

It is certified that error appears in the above-identified patent and that said Letters Patent is hereby corrected as shown below:

Title Page, Item (22) delete "Filed: Nov. 4, 2008" and insert --Aug. 26, 2008--.

Signed and Sealed this
Nineteenth Day of July, 2016

Michelle K. Lee
*Director of the United States Patent and Trademark Office*